US011085027B2

(12) United States Patent
Melton et al.

(10) Patent No.: US 11,085,027 B2
(45) Date of Patent: *Aug. 10, 2021

(54) SERUM-FREE IN VITRO DIRECTED DIFFERENTIATION PROTOCOL FOR GENERATING STEM CELL-DERIVED BETA CELLS AND USES THEREOF

(71) Applicant: President and Fellows of Harvard College, Cambridge, MA (US)

(72) Inventors: Douglas A. Melton, Lexington, MA (US); Mads Gurtler, Kongens Lyngby (DK)

(73) Assignee: President and Fellows of Harvard College, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/934,885

(22) Filed: Jul. 21, 2020

(65) Prior Publication Data

US 2020/0347357 A1 Nov. 5, 2020

Related U.S. Application Data

(63) Continuation of application No. 16/573,985, filed on Sep. 17, 2019, which is a continuation of application No. 14/975,158, filed on Dec. 18, 2015, now Pat. No. 10,443,042.

(60) Provisional application No. 62/094,010, filed on Dec. 18, 2014.

(51) Int. Cl.
C12N 5/071 (2010.01)

(52) U.S. Cl.
CPC ........ *C12N 5/0676* (2013.01); *C12N 2500/12* (2013.01); *C12N 2500/22* (2013.01); *C12N 2500/30* (2013.01); *C12N 2500/34* (2013.01); *C12N 2500/36* (2013.01); *C12N 2500/38* (2013.01); *C12N 2500/46* (2013.01); *C12N 2500/90* (2013.01); *C12N 2501/33* (2013.01); *C12N 2501/91* (2013.01)

(58) Field of Classification Search
CPC .................................................... C12N 5/0676
See application file for complete search history.

(56) References Cited

U.S. PATENT DOCUMENTS

| | | | |
|---|---|---|---|
| 4,391,909 A | 7/1983 | Lim | |
| 6,436,704 B1 | 8/2002 | Roberts et al. | |
| 6,667,176 B1 | 12/2003 | Funk et al. | |
| 6,800,480 B1 | 10/2004 | Bodnar et al. | |
| 7,033,831 B2 | 4/2006 | Fisk et al. | |
| 7,157,278 B2 | 1/2007 | Jin | |
| 7,297,539 B2 | 11/2007 | Mandalam et al. | |
| 7,326,572 B2 | 2/2008 | Fisk et al. | |
| 7,410,798 B2 | 8/2008 | Mandalam et al. | |
| 7,432,104 B2 | 10/2008 | Mitalipova et al. | |
| 7,510,876 B2 | 3/2009 | D'amour et al. | |
| 7,534,608 B2 | 5/2009 | Martinson et al. | |
| 7,541,185 B2 | 6/2009 | D'amour et al. | |
| 7,625,753 B2 | 12/2009 | Kelly et al. | |
| 7,695,963 B2 | 4/2010 | Agulnick et al. | |
| 7,695,965 B2 | 4/2010 | Martinson et al. | |
| 7,704,738 B2 | 4/2010 | D'amour et al. | |
| 7,964,402 B2 | 6/2011 | Terskikh et al. | |
| 7,985,585 B2 | 7/2011 | D'amour et al. | |
| 7,993,916 B2 | 8/2011 | Agulnick et al. | |
| 7,993,920 B2 | 8/2011 | Martinson et al. | |
| 8,008,075 B2 | 8/2011 | Green et al. | |
| 8,129,182 B2 | 3/2012 | D'amour et al. | |
| 8,153,429 B2 | 4/2012 | Robins et al. | |
| 8,187,878 B2 | 5/2012 | Dalton et al. | |
| 8,211,699 B2 | 7/2012 | Robins et al. | |
| 8,216,836 B2 | 7/2012 | D'amour et al. | |
| 8,278,106 B2 | 10/2012 | Martinson et al. | |
| 8,334,138 B2 | 12/2012 | Robins et al. | |
| 8,338,170 B2 | 12/2012 | Kelly et al. | |
| 8,415,153 B2 | 4/2013 | Majumdar et al. | |
| 8,445,273 B2 | 5/2013 | Green et al. | |
| 8,603,811 B2 | 12/2013 | D'amour et al. | |
| 8,623,645 B2 | 1/2014 | D'amour et al. | |
| 8,647,873 B2 | 2/2014 | D'amour et al. | |
| 8,658,151 B2 | 2/2014 | Kelly et al. | |
| 8,785,184 B2 | 7/2014 | Xu | |
| 8,785,185 B2 | 7/2014 | Xu et al. | |
| 8,859,286 B2 | 10/2014 | Agulnick et al. | |
| 9,096,832 B2 | 8/2015 | Xu | |
| 9,109,245 B2 | 8/2015 | Agulnick et al. | |
| 9,186,381 B2 | 11/2015 | Zender et al. | |

(Continued)

FOREIGN PATENT DOCUMENTS

| | | |
|---|---|---|
| EP | 1676574 | 7/2006 |
| EP | 1456356 | 12/2009 |

(Continued)

OTHER PUBLICATIONS

Greggio et al. (2013, Development, vol. 140, pp. 4452-4462) (Year: 2013).*
Xu et al. (2010, PNAS, vol. 107(18), pp. 8129-8134) (Year: 2010).*
Aguayo-Mazzucato, et al., "Mafa Expression Enhances Glucose-Responsive Insulin Secretion in Neonatal Rat Beta Cells," *Diabetologia*, 54(3):583-593, (Mar. 2011).
Aguayo-Mazzucato, et al., "Thyroid Hormone Promotes Postnatal Rat Pancreatic β-Cell Development and Glucose-Responsive Insulin Secretion Through MAFA," *Diabetes*, 62:1569-1580, (2013).

(Continued)

*Primary Examiner* — Thaian N. Ton
*Assistant Examiner* — David A Montanari
(74) *Attorney, Agent, or Firm* — Morse, Barnes-Brown & Pendleton, P.C.; Lisa M. Warren, Esq.

(57) ABSTRACT

Disclosed herein are methods for generating SC-β cells using chemically defined, completely serum free media, and isolated populations of SC-β cells for use in various applications, such as cell therapy.

22 Claims, 4 Drawing Sheets

(56) References Cited

U.S. PATENT DOCUMENTS

| | | |
|---|---|---|
| 9,650,610 B2 | 5/2017 | Agulnick |
| 9,974,784 B2 | 5/2018 | Groppe |
| 10,030,229 B2 | 7/2018 | Peterson et al. |
| 10,138,465 B2 | 11/2018 | Rezania |
| 10,253,298 B2 | 4/2019 | Melton et al. |
| 10,443,042 B2 | 10/2019 | Melton et al. |
| 10,927,350 B2 | 2/2021 | Melton et al. |
| 2001/0049130 A1 | 12/2001 | Spielberg |
| 2002/0094569 A1 | 7/2002 | Yu et al. |
| 2003/0138948 A1 | 7/2003 | Fisk et al. |
| 2004/0121460 A1 | 6/2004 | Lumelsky et al. |
| 2004/0191901 A1 | 9/2004 | Assady et al. |
| 2004/0259244 A1 | 12/2004 | Scharp et al. |
| 2005/0053588 A1 | 3/2005 | Yin |
| 2006/0040385 A1 | 2/2006 | Itskovitz-Eldor et al. |
| 2006/0040387 A1 | 2/2006 | Fisk et al. |
| 2006/0194321 A1 | 8/2006 | Colman et al. |
| 2008/0145889 A1 | 6/2008 | Fisk et al. |
| 2008/0299582 A1 | 12/2008 | Mandalam et al. |
| 2009/0170198 A1 | 7/2009 | Rezania |
| 2009/0263896 A1 | 10/2009 | Kelly et al. |
| 2009/0298178 A1 | 12/2009 | D'Amour |
| 2009/0325180 A1 | 12/2009 | Fisk et al. |
| 2010/0015100 A1 | 1/2010 | Xu |
| 2010/0015711 A1 | 1/2010 | Davis et al. |
| 2010/0112693 A1 | 5/2010 | Rezania et al. |
| 2010/0144033 A1 | 6/2010 | Mandalam et al. |
| 2010/0240130 A1 | 9/2010 | Majumdar et al. |
| 2010/0260728 A1 | 10/2010 | Martinson et al. |
| 2010/0311166 A1 | 12/2010 | Florio et al. |
| 2011/0008819 A1 | 1/2011 | Chipperfield et al. |
| 2011/0014702 A1 | 1/2011 | Xu |
| 2011/0053930 A1 | 3/2011 | Yu et al. |
| 2011/0151560 A1 | 6/2011 | Xu |
| 2011/0280842 A1 | 11/2011 | Melton et al. |
| 2011/0281355 A1 | 11/2011 | Xu |
| 2012/0009675 A1 | 1/2012 | Martinson et al. |
| 2012/0052571 A1 | 3/2012 | Fryer |
| 2012/0052575 A1 | 3/2012 | Rezania |
| 2012/0052576 A1 | 3/2012 | Rezania |
| 2012/0135015 A1 | 5/2012 | Noguchi et al. |
| 2012/0141436 A1 | 6/2012 | Bonner-Weir et al. |
| 2013/0034526 A1 | 2/2013 | Itskovitz-Eldor et al. |
| 2013/0071931 A1 | 3/2013 | Ishikawa |
| 2013/0189777 A1 | 7/2013 | Rezania |
| 2013/0316357 A1 | 11/2013 | D'amour et al. |
| 2013/0330823 A1 | 12/2013 | Rezania |
| 2013/0337564 A1 | 12/2013 | Davis et al. |
| 2014/0080210 A1 | 3/2014 | Davis et al. |
| 2014/0134726 A1 | 5/2014 | D'amour et al. |
| 2014/0154801 A1 | 6/2014 | D'amour et al. |
| 2014/0154802 A1 | 6/2014 | Robins et al. |
| 2014/0162359 A1 | 6/2014 | Rezania |
| 2014/0186305 A1 | 7/2014 | Rezania |
| 2014/0186948 A1 | 7/2014 | Schulz et al. |
| 2014/0186953 A1 | 7/2014 | Rezania |
| 2014/0193902 A1 | 7/2014 | D'amour et al. |
| 2014/0193904 A1 | 7/2014 | D'amour et al. |
| 2014/0242693 A1 | 8/2014 | Fryer et al. |
| 2014/0287944 A1 | 9/2014 | Hrvatin et al. |
| 2014/0329704 A1 | 11/2014 | Melton et al. |
| 2014/0335611 A1 | 11/2014 | Chen et al. |
| 2015/0218522 A1 | 8/2015 | Peterson et al. |
| 2015/0240212 A1 | 8/2015 | Peterson et al. |
| 2015/0247123 A1 | 9/2015 | Ekberg et al. |
| 2015/0329828 A1 | 11/2015 | Rezania |
| 2015/0376574 A1 | 12/2015 | Talavera-Adame et al. |
| 2016/0022742 A1 | 1/2016 | Zender et al. |
| 2016/0175363 A1 | 6/2016 | Melton et al. |
| 2016/0177267 A1 | 6/2016 | Melton et al. |
| 2016/0177268 A1 | 6/2016 | Melton et al. |
| 2016/0177269 A1 | 6/2016 | Melton et al. |
| 2016/0186143 A1 | 6/2016 | Melton et al. |
| 2016/0208215 A1 | 7/2016 | Doehn et al. |
| 2017/0029778 A1 | 2/2017 | Peterson et al. |
| 2017/0233700 A1 | 8/2017 | Kunisada et al. |
| 2017/0240866 A1 | 8/2017 | Wells et al. |

FOREIGN PATENT DOCUMENTS

| | | | |
|---|---|---|---|
| EP | 2267116 | 12/2010 | |
| EP | 2283117 | 2/2011 | |
| EP | 2292734 | 3/2011 | |
| EP | 2341147 | 6/2011 | |
| EP | 2377922 | 10/2011 | |
| EP | 2569419 | 11/2011 | |
| EP | 2650359 | 10/2013 | |
| EP | 2650360 | 10/2013 | |
| EP | 2664669 | 11/2013 | |
| EP | 2674485 | 12/2013 | |
| JP | HEI-11-505411 | 5/1999 | |
| JP | 2006-506047 | 2/2006 | |
| JP | 2016-503654 | 2/2016 | |
| JP | 2016-506246 | 3/2016 | |
| RU | 2011121843 | 12/2012 | |
| WO | WO 1996/031242 | 10/1996 | |
| WO | WO 1999/020740 | 4/1999 | |
| WO | WO 2001/088104 | 11/2001 | |
| WO | WO 2002/042445 | 5/2002 | |
| WO | WO 2003/100026 | 5/2003 | |
| WO | WO 2003/050249 | 6/2003 | |
| WO | WO 2004/058764 | 7/2004 | |
| WO | WO 2007/002136 | 1/2007 | |
| WO | WO 2007/075807 | 7/2007 | |
| WO | WO 2007/103282 | 9/2007 | |
| WO | WO 2007/127927 | 11/2007 | |
| WO | WO 2008/083331 | 7/2008 | |
| WO | WO 2008/102000 | 8/2008 | |
| WO | WO 2009/012428 | 1/2009 | |
| WO | WO 2009/018453 | 2/2009 | |
| WO | WO 2009/070592 | 6/2009 | |
| WO | WO 2010/057039 | 5/2010 | |
| WO | WO 2010/059778 | 5/2010 | |
| WO | WO 2011/059725 | 5/2011 | |
| WO | WO 2011/079017 | 6/2011 | |
| WO | WO 2011/109279 | 9/2011 | |
| WO | WO 2011/123572 | 10/2011 | |
| WO | WO-2011/139628 A1 | 11/2011 | |
| WO | WO 2012/020845 | 2/2012 | |
| WO | WO 2012/021698 | 2/2012 | |
| WO | WO 2012/025725 | 3/2012 | |
| WO | WO 2012/030540 | 3/2012 | |
| WO | WO 2012/168930 | 12/2012 | |
| WO | WO 2013/057164 | 4/2013 | |
| WO | WO 2013/095953 | 6/2013 | |
| WO | WO-2013095953 A1 * | 6/2013 | ........... C12N 5/0676 |
| WO | WO 2014/033322 | 3/2014 | |
| WO | WO 2014/105543 | 7/2014 | |
| WO | WO 2014/105546 | 7/2014 | |
| WO | WO 2014/151871 | 9/2014 | |
| WO | WO 2014/160413 | 10/2014 | |
| WO | WO 2014/201167 | 12/2014 | |
| WO | WO 2015/002724 | 1/2015 | |
| WO | WO 2015/028614 | 3/2015 | |
| WO | WO 2015/175307 | 11/2015 | |
| WO | WO 2016/100898 | 6/2016 | |
| WO | WO 2016/100909 | 6/2016 | |
| WO | WO 2016/100921 | 6/2016 | |
| WO | WO 2016/100925 | 6/2016 | |
| WO | WO 2016/100930 | 6/2016 | |

OTHER PUBLICATIONS

Amariglio, et al., "Donor-Derived Brain Tumor Following Neural Stem Cell Transplantation in an Ataxia Telangiectasia Patient," *PLOS Medicine*, 6(2):1-3, (2009). (2 pages of translation of relevance).

Apelqvist, et al., "Notch Signaling Controls Pancreatic Cell Differentiation," *Nature*, 400:877-881, (1999).

Ashery-Padan et al., "Conditional Inactivation of Pax6 in The Pancreas Causes Early Onset of Diabetes," *Developmental Biology*, 269:479-488, (2004).

(56) References Cited

OTHER PUBLICATIONS

Assady, et al., "Insulin Production by Human Embryonic Stem Cells," Diabetes, 50:1691-1697, (Aug. 2001).
Baetge, et al., "Production of β-Cells From Human Embryonic Stem Cells," Diabetes, Obesity and Metabolism, 10:186-194, (2008).
Basford, et al., "The Functional and Molecular Characterisation of Human Embryonic Stem Cell-Derived Insulin-Positive Cells Compared With Adult Pancreatic Beta Cells," Diabetologia, 55:358-371, (2012).
Beattie, et al., "Sustained Proliferation of PDX-1+ Cells Derived From Human Islets," Diabetes, 48: 1013-1019, (May 1999).
Bellin, et al., "Potent Induction Immunotherapy Promotes Long-Term Insulin Independence After Islet Transplantation in Type 1 Diabetes," Am. J. Transplant., 12:1576-1583, (2012).
Bennett, et al., "SP600125, An Anthrapyrazolone Inhibitor of Jun N-Terminal Kinase," PNAS, 98(24):13681-13686, (Nov. 20, 2001).
Blazhevich, et al., "Cell Culturing: Lecture Course," 6 pages (1 page of translation of relevance) (2004).
Boretti, et al., "Induced Cell Clustering Enhances Islet Beta Cell Formation From Human Cultures Enriched for Pancreatic Ductal Epithelial Cells," Tissue Eng., 12(4):939-948, (2006).
Boretti, et al., "Induced Cell Clustering Enhances Islet Beta Cell Formation From Human Cultures Enriched for Pancreatic Ductal Epithelial Cells," 2003 Summer Bioengineering Conference, Jun. 25-29, Sonesta Beach Report in Key Biscayne, Florida, 2 pages.
Bose, et al., "Human Embryonic Stem Cell Differentiation Into Insulin Secreting Beta-Cells For Diabetes," Cell Biol Int., 36(11):1013-1020, (2012).
Brolen, et al., "Signals From the Embryonic Mouse Pancreas Induce Differentiation of Human Embryonic Stem Cells Into Insulin-Producing β-cell-like Cells," Diabetes, 54:2867-2874, (2005).
Campbell-Thompson, et al., "Collection Protocol for Human Pancreas," Journal of Visualized Experiments, 63:1-5, (May 2012).
Cerf, "Transcription Factors Regulating β-cell Function," European Journal of Endocrinology, 155:671-679, (2006).
Chakrabarti, et al., "Transcription Factors Direct the Development and Function of Pancreatic Beta Cells," Trends Endocrinol Metab., 14(2):78-84, (Mar. 2003).
Chen, et al., "Scalable GMP Compliant Suspension Culture System for Human ES Cells," Stem Cell Research, 8:388-402, (2012).
Cheng, et al., "Self-Renewing Endodermal Progenitor Lines Generated From Human Pluripotent Stem Cells," Cell Stem Cell, 10:371-384, (2012).
Chiang, et al., "Single-Cell Transcript Analysis of Pancreas Development," Dev. Cell., 4(3):383-393, (Mar. 2003).
Choi, et al., "A Comparison of Genetically Matched Cell Lines Reveals the Equivalence of Human iPSCs and ESCs," Nat. Biotechnol., Oct. 26, 2015. doi: 10.1038/nbt.3388. [Epub ahead of print].
CMRL-1066 Data Sheet. Retrieved online Sep. 30, 2017. https://www.sigmaaldrich.com/content/dam/sigma-aldrich/docs/sigma/datasheet/c0422dat.pdf (1998).
Cohen, et al., "Antibiotics Reduce the Growth Rate and Differentiation of Embryonic Stem Cell Cultures," Tissue Eng., 12(7):2025-2030, (2006).
Corkey, et al., "A Role for Malonyl-CoA in Glucose-Stimulated Insulin Secretion from Clonal Pancreatic β-Cells," J. Biol. Chem., 254(36):21608-21612, (Dec. 1989).
D'Amour, et al., "Efficient Differentiation of Human Embryonic Stem Cells to Definitive Endoderm," Nat. Biotechnol., 23(12):1534-1541, (2005).
D'Amour, et al., "Production of Pancreatic Hormone-Expressing Endocrine Cells From Human Embryonic Stem Cells," Nat. Biotechnol., 24(11):1392-1401, (2006).
Docherty, "Pancreatic Stellate Cells Can Form New β-Like Cells," Biochem, J., 421:e1-e4, (2009).
Dror, et al., "Notch Signaling Suppresses Apoptosis in Adult Human and Mouse Pancreatic Islet Cells," Diabetlogia 50:2504-2515, (2007).

Eberhardt, et al., "Multipotential Nestin and Isl-1 Positive Mesenchymal Stem Cells Isolated From Human Pancreatic Islets," Biochem. Biophys. Res. Commun., 345(3)1167-1176, (2006).
Falzacappa, et al., "3,5,3'-Triiodothyronine (T3) is a Survival Factor for Pancreatic Beta-Cells Undergoing Apoptosis," J. Cell Physiol., 206(2):309-321, (Feb. 2006).
Greggio, et al., "Artificial Three-Dimensional Niches Deconstruct Pancreas Development in vitro," Development, 140:4452-4462, (2013).
Habener, et al., "Minireview: Transcriptional Regulation in Pancreatic Development," Endocrinology, 146(3):1025-1034, (2004).
Hanley, "Closing in on Pancreatic Beta Cells," Nature Biotechnology, 32(11):1100-1102, (Nov. 2014).
Haycock, "3D Cell Culture: A Review of Current Approaches and Techniques," Molecular Biology, 695:1-15, (2011).
Heremans, et al., "Recapitulation of Embryonic Neuroendocrine Differentiation in Adult Human Pancreatic Duct Cells Expressing Neurogenin 3," The Journal of Cell Biology, 159(2):303-311, (Oct. 2002).
Hernandez, et al., "Microcapsules and Microcarriers for in Situ Cell Delivery," Advanced Drug Delivery Reviews, 62:711-730, (2010).
Hrvatin et al., "Differentiated Human Stem Cells Resemble Fetal, Not Adult, β-cells," PNAS, 111(8):3038-3043, (2014).
Hur, et al., "New Method to Differentiate Human Peripheral Blood Monocytes into Insulin Producing Cells: Human Hematosphere Culture," Biochemical and Biophysical Research Communications, 418:765-769, (2012).
Huynh, et al., "Screening and Identification of a Novel Class of TGF-β Type 1 Receptor Kinase Inhibitor," Society for Laboratory Automation and Screening, 16(7):724-733, (2011).
Isayeva, et al., "Characterization and Performance of Membranes Designed for Macroencapsulation/Implantation of Pancreatic Islet Cells," Biomaterials, 24(20):3483-3491, (2003).
Jahansouz, et al., "Evolution of β-Cell Replacement Therapy in Diabetes Mellitus: Islet Cell Transplantation," Journal of Transplantation, pp. 1-21, (2011).
Jeon, et al., "Differentiation and Transplantation of Functional Pancreatic Beta Cells Generated from Induced Pluripotent Stem Cells Derived from a Type 1 Diabetes Mouse Model," Stem Cells Dev., 21(14):2642-2655, (2012).
Jiang, et al., "In vitro Derivation of Functional Insulin-Producing Cells from Human Embryonic Stem Cells," Cell Research, 17(4):333-344, (2007).
Kozhucharova, et al., "Novel Human Embryonic Stem Cell Lines C612 and C910," Cytology, 51(7):551-558, (2009). (2 pages of translation of relevance).
Kroon, et al., "Pancreatic Endoderm Derived From Human Embryonic Stem Cell Generates Glucose-Responsive Insulin-Secreting Cells In Vivo," Nat. Biotechnol., 26(4):443-452, (Apr. 2008).
Kumar, et al., "Recent Developments in β-Cell Differentiation of Pluripotent Stem Cells Induced by Small and Large Molecules," Int. J. Mol. Sci., 15(12):23418-23447, (2014).
Kumar, et al., "Signals From Lateral Plate Mesoderm Instruct Endoderm Toward A Pancreatic Fate," Dev. Biol., 259(1):109-122, (Jul. 2003).
Kunisada, et al., "Small Molecules Induce Efficient Differentiation Into Insulin-Producing Cells From Human Induced Pluripotent Stem Cells," Stem Cell Research, 8:274-284, (2012).
Lee, et al., "All-Trans-Retinoic Acid as a Novel Therapeutic Strategy for Alzheimer's Disease," Expert Rev. Neurother, 9(11):1615-1621, (2009).
Lim, et al., Microencapsulated Islets as Bioartificial Endocrine Pancreas, Science, 210(4472):908-910, (Nov. 21, 1980).
Lin, et al., "Transforming Growth Factor-β/Smad3 Signaling Regulates Insulin Gene Transcription and Pancreatic Islet β-Cell Function," The Journal of Biological Chemistry, 284(18):12246-12257, (May 1, 2009).
Lumelsky, et al., "Differentiation of Embryonic Stem Cells to Insulin-Secreting Structures Similar to Pancreatic Islets," Science, 292:1389-1394, (2001).
Madsen, et al., "Towards Cell Therapy For Diabetes," Nat. Biotechnol., 24(12):1481-1483, (Dec. 2006).

(56) References Cited

OTHER PUBLICATIONS

Maehr, et al., "Generation of Pluripotent Stem Cells From Patients With Type 1 Diabetes," *PNAS*, 106(37):15768-15773, (2009).
Manning, et al., "The Protein Kinase Complement of the Human Genome," *Science*, 298:1912-1934, (Dec. 6, 2002).
Marzorati, et al., "Culture Medium Modulates Proinflammatory Conditions of Human Pancreatic Islets Before Transplantation," *Am. J. Transplant*, 6(11):2791-2795, (2006).
Matschinsky, "Assessing the Potential of Glucokinase Activators in Diabetes Therapy," *Nature Reviews Drug Discovery*, 8:399-416, (2009).
McLean, et al., "Activin A Efficiently Specifies Definitive Endoderm From Human Embryonic Stem Cells Only When Phosphatidylinositol 3-Kinase Signaling is Suppressed," *Stem Cells*, 25(1):29-38, (Jan. 2007).
McQuilling, et al., "New Alginate Microcapsule System for Angiogenic Protein Delivery and Immunoisolation of Islets for Transplantation in the Rat Omentum Pouch," *Transplantation Proceedings*, 43(9):3262-3264, (Nov. 2011).
Michael, et al., "Pancreatic β-cells Secrete Insulin in Fast-And Slow-Release Forms," *Diabetes*, 55: 600-607, (2006).
Moens, et al., "Dual Glucagon Recognition by Pancreatic Beta-Cells Via Glucagon and Glucagon-Like Peptide 1 Receptors," *Diabetes*, 47:66-72, (1998).
Mollard, et al., "Design, Synthesis, and Biological Evaluation of a Series of Novel AXL Kinase Inhibitors," *ACS Medicinal Chemistry Letters*, 2:907-912, (2011).
Motté, et al., "Composition and Function of Macroencapsulated Human Embryonic Stem Cell-Derived Implants: Comparison With Clinical Human Islet Cell Grafts," *American Journal of Physiology-Endocrinology and Metabolism*, 307(9):E838-E846, (2004).
Mudduluru, et al., "Regulation of Axl Receptor Tyrosine Kinase Expression by miR-34a and miR-199a/b in Solid Cancer," *Oncogene*, 30(25):2889-2899, (2011).
Murua, et al., "Cell Microencapsulation Technology: Towards Clinical Application," *Journal of Controlled Release*, 132(2):76-83, (2008).
Narayanan, et al., "Extracellular Matrix-Mediated Differentiation of Human Embryonic Stem Cells: Differentiation to Insulin-Secreting Beta Cells," *Tissue Engineering: Part A*, 20(1-2):424-433, (2013).
Natalicchio, et al., "Exendin-4 Protects Pancreatic Beta Cells from Palmitate-Induced Apoptosis by Interfering with GPR40 and the MKK4/7 Stress Kinase Signaling Pathway," *Diabetologia*, 56:2456-2466, (2013).
Nishimura, et al., "A Switch from MafB to MafA Expression Accompanies Differentiation to Pancreatic β-Cells," *Developmental Biology*, 293:526-539, (2006).
Nostro, et al., "Generation of Beta Cells From Human Pluripotent Stem Cells: Potential for Regenerative Medicine," *Seminars in Cell & Developmental Biology*, 23:701-710, (2012).
Nostro, et al., "Stage-Specific Signaling Through TGFβ Family Members and WNT Regulates Patterning and Pancreatic Specification of Human Pluripotent Stem Cells," *Development*, 138:861-871, (2011).
O'Brien, et al., "Suspended in Culture—Human Pluripotent Cells for Scalable Technologies," *Stem Cell Research*, 9:167-170, (2012).
Orive, et al., "Application of Cell Encapsulation for Controlled Delivery of Biological Therapeutics," *Advanced Drug Delivery Reviews*, pp. 1-12, (2013).
Pagliuca, et al., "How to Make a Functional β-cell," *Development*, 140:2472-2483, (2013).
Pagliuca, et al., "Generation of Functional Human Pancreatic β Cells In Vitro," *Cell*, 159(2):428-439, (Oct. 2014).
Parsons, et al., "Notch-Responsive Cells Initiate the Secondary Transition in Larval Zebrafish Pancreas," *Mechanisms of Development*, 126(10):898-912, (2009).
Phillips, et al., "Directed Differentiation of Human Embryonic Stem Cells into the Pancreatic Endocrine Lineage," *Stem Cells and Dev.*, 16:561-578, (2007).
Piran, et al., "Pharmacological Induction of Pancreatic Islet Cell Transdifferentiation; Relevance to Type I Diabetes," *Cell Death and Disease*, 5(e1357):1-36, (2014).
Qi, et al., "PVA Hydrogel Sheet Macroencapsulation of the Bioartificial Pancreas," *Biomaterials*, 24(27):5885-5892, (2004).
Ratanasavanh, et al., "Immunocytochemical Evidence for the Maintenance of Cytochrome P-450 Isozymes, NADPH Cytochrome C Reductase, and Epoxide Hydrolase in Pure and Mixed Primary Cultures of Adult Human Hepatocytes," *J. Histochem. Cytochem.*, 34(4):527-533, (Apr. 1986).
Rathaore, et al., "Microencapsulation of Microbial Cells," *Journal of Food Engineering*, 116:369-381, (2013).
Ravassard, et al., "A Genetically Engineered Human Pancreatic β Cell Line Exhibiting Glucose-Inducible Insulin Secretion," *The Journal of Clinical Investigation*, 121(9):3589-3597, (2011).
Rezania, et al., "Enrichment of Human Embryonic Stem Cell-Derived NKX6.1-Expressing Pancreatic Progenitor Cells Accelerates the Maturation of Insulin-Secreting Cells In Vivo," *Stem Cells*, 31:2432-2442, (2013).
Rezania, et al., "Maturation of Human Embryonic Stem Cell-Derived Pancreatic Progenitors Into Functional Islets Capable of Treating Pre-Existing Diabetes in Mice," *Diabetes*, 61:2016-2029, (2012).
Rezania, et al., "Production of Functional Glucagon-Secreting α-cells From Human Embryonic Stem Cells," *Diabetes*, 60:239-247, (Jan. 2011).
Rezania, et al., "Reversal of Diabetes With Insulin-Producing Cells Derived In Vitro from Human Pluripotent Stem Cells," *Nat. Biotechnol.*, 21(11):1121-1133, (Nov. 2014).
Roche, "Protocols to Differentiate Embryonic Stem Cells Into Insulin Producing Cells," *Av. Diabetol.*, 24(2):128-137, (2008).
Rovira, et al., "Chemical Screen Identifies FDA-Approved Drugs and Target Pathways That Induce Precocious Pancreatic Endocrine Differentiation," *Proc. Natl. Acad. Sci. U.S.A.*, 108(48):19264-19269, (2011).
Sander, et al., "Homeobox Gene Nkx6.1 Lies Downstream of Nkx2.2 in the Major Pathway of β-cell Formation in the Pancreas," *Development*, 127:5533-5540, (2000).
Sander, et al., "The β-cell Transcription Factors and Development of the Pancreas," *J. Mol. Med.*, 75:327-340, (1997).
Schuldiner, et al., "Effects of Eight Growth Factors on the Differentiation of Cells Derived From Human Embryonic Stem Cells," *Proc. Natl. Acad. Sci. U.S.A.*, 97(21):11307-11312, (Oct. 2000).
Schulz, et al., "A Scalable System for Production of Functional Pancreatic Progenitors From Human Embryonic Stem Cells," *PLoS One*, 7(5):1-17, (May 2012).
Schumacher, et al., "Staurosporine is a Potent Activator of Neuronal, Glial, and "CNS Stem Cell-Like" Neurosphere Differentiation in Murine Embryonic Stem Cells," *Molecular and Cellular Neuroscience*, 23:669-680, (2003).
Segrev, et al., "Differentiation of Human Embryonic Stem Cells into Insulin-Producing Clusters," *Stem Cells*, 22:265-274, (2004).
Shaer, et al., "Differentiation of Human-Induced Pluripotent Stem Cells Into Insulin-Producing Clusters," *Exp. Clin. Transplant*, 13(1):68-75, (2014).
Shahjalal, et al., "Generation of Insulin-Producing β-Like Cells from Human iPS Cells in a Defined and Completely Xeno-Free Culture System," *Journal of Molecular Cell Biology*, 6(5):394-408, (2014).
Shapiro, et al., "International Trial of the Edmonton Protocol for Islet Transplantation," *N. Engl. J. Med.*, 355:1318-1330, (2006).
Shi, et al., "Inducing Embryonic Stem Cells to Differentiate into Pancreatic β-cells by a Novel Three-Step Approach with Activin A and All-Trans Retinoic Acid," *Stem Cells* 23:656-662, (2005).
Shim, et al., "Directed Differentiation of Human Embryonic Stem Cells Towards a Pancreatic Cell Fate," *Diabetologia*, 50:1128-1238, (2007).
Sneddon, et al., "Self-Renewal of Embryonic-Stem-Cell-Derived Progenitors by Organ-Matched Mesenchyme," *Nature*, 491:765-768, (2012).
SoRelle, et al., "Beta Cell Replacement Therapy," *Type 1 Diabetes—Pathogenesis, Genetics and Immunotherapy*, 22:503-526, (2011).

(56) References Cited

OTHER PUBLICATIONS

Soria, "In-vitro Differentiation of Pancreatic β-cells," *Differentiation*, 68:205-219, (2001).
Spence, et al., "Sox17 Regulates Organ Lineage Segregation of Ventral Foregut Progenitor Cells," *Dev. Cell.*, 17(1):62-74, (Jul. 2009).
Sui, et al., "Stem Cell Therapy for Diabetes: A Call for Efficient Differentiation of Pancreatic Progenitors," *J. Regen. Med.* 2(1):1-4, (2013).
Taylor, et al., "NKX6-I Is Essential for Maintaining the Functional State of Pancreatic Beta Cells," *Cell Rep*, 4:1262-1275, (2013).
Thatava, et al., "Indolactam V/GLP-1-Mediated Differentiation of Human iPS Cells into Glucose-Responsive Insulin-Secreting Progeny," *Gene Ther.*, 18(3):283-293, (2011).
ThermoFisher Scientific, "B-27 Serum-Free Supplement (50X) liquid," ThermoFisher Scientific Website, Retrieved from the Internet: URL:https://www.thermofisher.com/nl/en/home/technical-resources/media-formulation.250.html, on Jun. 13, 2016.
Thowfeequ, et al., "Betacellulin Inhibits Amylase and Glucagon Production and Promotes Beta Cell Differentiation in Mouse Embryonic Pancreas," *Diabetologia*, 50:1688-1697, (2007).
Treff, et al., "Differentiation of Embryonic Stem Cells Conditionally Expressing Neurogenin 3," *Stem Cells*, 24(11):2529-2537, (1999).
Tsaniras, et al., "Generating Pancreatic βCells from Embryonic Stem Cells by Manipulating Signaling Pathways," *Journal of Endocrinology*, 206:13-26, (2010).
Tsuchida, et al., "Activin Signaling as an Emerging Target for Therapeutic Interventions," *Cell Communication & Signaling*, 7(15):1-11, (2009).
Wachs, et al., "High Efficacy of Clonal Growth and Expansion of Adult Neural Stem Cells," *Laboratory Investigation*, 83(7):949-962, (Jul. 2003).
Xie, et al., "Dynamic Chromatin Remodeling Mediated by Polycomb Proteins Orchestrates Pancreatic Differentiation of Human Embryonic Stem Cells," *Cell Stem Cell*, 12:224-237, (2013).
Zanin, et al., "The Development of Encapsulated Cell Technologies as Therapies for Neurological and Sensory Diseases," *Journal of Controlled Release*, 160:3-13, (2012).
Zhdanov, et al., "The Secrets of the Third Kingdom," *Publishing House "Znanie" Moscow*:pp. 124-125, (1975). (2 pages of translation).
Zhu, et al., "Generation of Pancreatic Insulin-Producing Cells from Rhesus Monkey Induced Pluripotent Stem Cells," *Diabetologia*, 54:2325-2336, (2011).
Zhu, et al., "Preventive Effect Of Notch Signaling Inhibition By a γ-Secretase Inhibitor On Peritoneal Dialysis Fluid-Induced Peritoneal Fibrosis In Rats," *American Journal of Pathology*, 176(2):650-659, (2010).
Zulewski, "Stem Cells with Potential to Generate Insulin-Producing Cells in Man," *Swiss Med. Wkly*, 136:647-654, (2006).
Zweigerdt, et al., "Scalable Expansion of Human Pluripotent Stem Cells in Suspension Culture," *Nature Protocols*, 6(5):689-700, (2011).
International Search Report for International Application PCT/US2014/041988, dated Dec. 24, 2014.
International Search Report for International Application PCT/US2014/041992, dated Oct. 24, 2014.
International Search Report for International Application PCT/US2015/066900, dated Mar. 3, 2016.
International Search Report for International Application PCT/US2015/066888, dated Feb. 26, 2016.
International Search Report for International Application PCT/US2015/066881, dated Mar. 3, 2016.
International Search Report for International Application PCT/US2015/066858, dated Mar. 11, 2016.
International Search Report for International Application PCT/US2015/066840, dated Mar. 31, 2016.
Supplementary European Search Report for European Application EP 14 81 0778, dated Sep. 28, 2016.
Supplementary European Search Report for European Application EP 14819763.5, dated Jan. 26, 2017.
Extended European Search Report for European Application EP 14819763.5, dated May 23, 2017.
Non-Final Office Action for U.S. Appl. No. 14/684,129, dated Sep. 4, 2015.
Final Office Action for U.S. Appl. No. 14/684,129, dated Mar. 8, 2016.
Non-Final Office Action for U.S. Appl. No. 14/684,101, dated Aug. 25, 2015.
Final Office Action for U.S. Appl. No. 14/684,101, dated Jan. 28, 2016.
Non-Final Office Action from U.S. Appl. No. 14/975,421, dated Sep. 15, 2016.
Advisory Action Before the Filing of an Appeal Brief for U.S. Appl. No. 14/684,101, dated Sep. 1, 2016.
Advisory Action Before the Filing of an Appeal Brief for U.S. Appl. No. 14/684,129, dated Nov. 9, 2016.
Non-Final Office Action for U.S. Appl. No. 14/975,383, dated Feb. 1, 2017.
Non-Final Office Action for U.S. Appl. No. 14/975,421, dated Mar. 1, 2017.
Non-Final Office Action for U.S. Appl. No. 14/684,129, dated May 8, 2017.
Non-Final Office Action for U.S. Appl. No. 14/684,101, dated Jun. 1, 2017.
Non-Final Office Action for U.S. Appl. No. 14/975,255, dated Jul. 17, 2017.
Non-Final Office Action for U.S. Appl. No. 14/975,158, dated Sep. 13, 2017.
Non-Final Office Action for U.S. Appl. No. 14/898,015, dated Oct. 13, 2017.
Non-Final Office Action for U.S. Appl. No. 14/975,457, dated Aug. 10, 2017.
Final Office Action for U.S. Appl. No. 14/684,101, dated Jan. 16, 2018.
Final Office Action for U.S. Appl. No. 14/684,129, dated Mar. 9, 2018.
Final Office Action for U.S. Appl. No. 14/975,457, dated Apr. 19, 2018.
Non-Final Office Action for U.S. Appl. No. 14/975,255, dated Apr. 12, 2018.
Notice of Allowance for U.S. Appl. No. 14/684,101, dated May 4, 2018.
Final Office Action for U.S. Appl. No. 14/975,457, dated May 23, 2018.
Final Office Action for U.S. Appl. No. 14/975,158, dated Jun. 28, 2018.
Final Office Action for U.S. Appl. No. 14/898,015, dated Aug. 10, 2018.
Non-Final Office Action for U.S. Appl. No. 14/975,457, dated Aug. 7, 2018.
Notice of Allowance for U.S. Appl. No. 14/975,255, dated Sep. 6, 2018.
Non-Final Office Action for U.S. Appl. No. 16/042,917, dated Dec. 3, 2018.
Notice of Allowance for U.S. Appl. No. 14/975,457, dated Nov. 23, 2018.
Non-Final Office Action for U.S. Appl. No. 15/666,555, dated Feb. 4, 2019.
Non-Final Office Action for U.S. Appl. No. 14/684,129, dated Apr. 16, 2019.
Notice of Allowance for U.S. Appl. No. 16/042,917, dated Aug. 26, 2019.
Notice of Allowance for U.S. Appl. No. 16/042,917, dated Sep. 20, 2019.
Notice of Allowance for U.S. Appl. No. 16/042,917, dated Dec. 18, 2019.
Notice of Allowance for U.S. Appl. No. 16/042,917, dated Dec. 31, 2019.
Notice of Allowance for U.S. Appl. No. 14/975,158, dated Jun. 3, 2019.

(56) References Cited

OTHER PUBLICATIONS

Notice of Allowance for U.S. Appl. No. 16/042,917, dated Jul. 17, 2019.
Third Party Submission from U.S. Appl. No. 16/042,933, dated Jul. 19, 2019.
Final Office Action for U.S. Appl. No. 15/666,555, dated Oct. 9, 2019.
Final Office Action for U.S. Appl. No. 14/684,129, dated Jan. 31, 2020.
Non-Final Office Action for U.S. Appl. No. 16/213,950, dated May 19, 2020.
Notice of Allowance for U.S. Appl. No. 16/934,333, dated Feb. 9, 2021.
Cai, et al., "Generation of Homogeneous PDX1+ Pancreatic Progenitors from Human ES Cell-Derived Endoderm Cells," *Journal of Molecular Cell Biology*, 2:50-60, (2010).
Ropiquet, et al., "FGF7/KGF Triggers Cell Transformation and Invasion on Immortalised Human Prostatic Epithelial PNT1A Cells," *Int. J. Cancer*, 82:237-243 (1999).
Zhang, et al., "Highly Efficient Differentiation of Human ES Cells and iPS Cells Into Mature Pancreatic Insulin-Producing Cells," *Cell Research*, 19:429-438, (2009).
Non-Final Office Action for U.S. Appl. No. 16/042,933, dated Dec. 30, 2020.
Non-Final Office Action for U.S. Appl. No. 16/934,503, dated Jan. 19, 2021.
Axxora.com Product Search Results for "Alk5 Inhibitor." Retrieved from URL: https://www.axxora.com/product-listing/ on Oct. 21, 2020 (Year: 2020).
Hrvatin, Ph.D. Dissertation, Harvard University, Dec. 2012. Accessible at http://nrs.harvard.edu/um-3:HUL.InstRepos:10433470 (Year: 2012).
Roskoski, "A Historical Overview of Protein Kinases and Their Targeted Small Molecule Inhibitors," Pharmacological Res., 100:1-23, (2015).
Tian, et al., "Protein Kinase C and Calcium Regulation of Adenylyl Cyclase in Isolated Rat Pancreatic Islets," Diabetes, 50:2505-2513, (2001).
Notice of Allowance for U.S. Appl. No. 16/213,950 dated Oct. 23, 2020.
Non-Final Office Action for U.S. Appl. No. 16/934,333, dated Oct. 26, 2020.
Non-Final Office Action for U.S. Appl. No. 16/934,764, dated Nov. 13, 2020.
Non-Final Office Action for U.S. Appl. No. 16/934,848, dated Nov. 13, 2020.
Non-Final Office Action for U.S. Appl. No. 16/934,412, dated Mar. 30, 2021.
Non-Final Office Action for U.S. Appl. No. 16/292,231, dated Mar. 26, 2021.
Notice of Allowance for U.S. Appl. No. 16/934,764, dated Apr. 15, 2021.
Final Office Action for U.S. Appl. No. 16/934,848, dated Mar. 17, 2021.
Notice of Allowance for U.S. Appl. No. 16/934,848, dated Apr. 23, 2021.
Notice of Allowance for U.S. Appl. No. 16/934,503 dated May 5, 2021.

\* cited by examiner

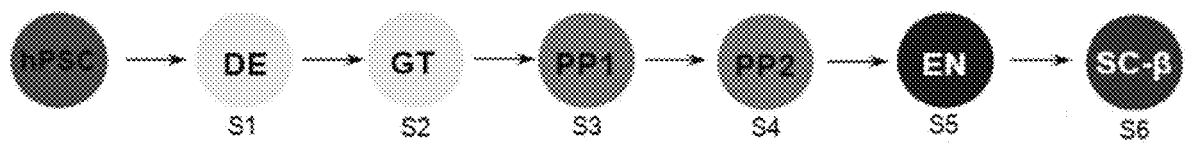
FIG. 2A
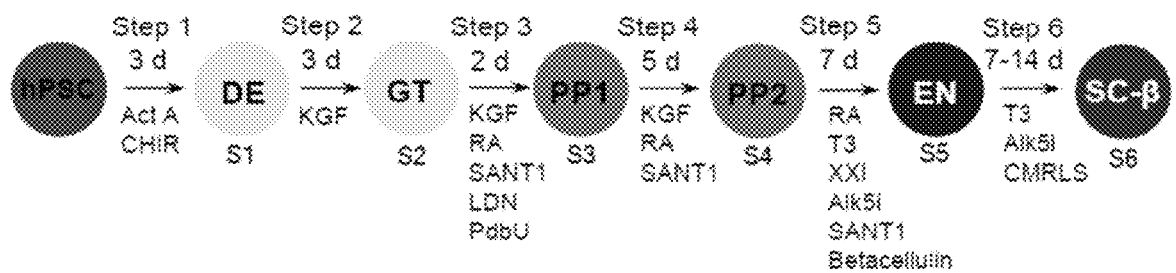
FIG. 2B
FIGS. 2A – 2B

| | Stage 1 | Stage 2 | Stage 3 | Stage 4 | Stage 5 | Stage 6 |
|---|---|---|---|---|---|---|
| Basal media | MCDB131 | MCDB131 Wash step with S1 | MCDB131 | MCDB131 | MCDB131 | CMRL5 |
| | 1% Pen/Strep | 1% Pen/Strep | 1% Pen/Strep | 1% Pen/Strep | 1% Pen/Strep | 1% Pen/Strep |
| | 2.5g/L NaHCO3 | 1.23g/L NaHCO3 | 1.23g/L NaHCO3 | 1.23g/L NaHCO3 | 1.75g/L NaHCO3 | |
| | 2mM Glutamax | 2mM Glutamax | 2mM Glutamax | 2mM Glutamax | 2mM Glutamax | |
| Supplement | 2% FAF-BSA | 2% FAF-BSA | 2% FAF-BSA | 2% FAF-BSA | 2% FAF-BSA | 10% Hyclone FBS |
| | 1:50,000 ITS-X | 1:50,000 ITS-X | 1:200 ITS-X | 1:200 ITS-X | 1:200 ITS-X | |
| | 8mM Glucose | 8mM Glucose | 8mM Glucose | 8mM Glucose | 25mM Glucose | |
| | 0.25mM Vit C | 0.25mM Vit C | 0.25mM Vit C | 0.25mM Vit C | 0.25mM Vit C | |
| Growth factors | 100ng/ml ActivinA | 50ng/ml KGF | 50ng/ml KGF | 50ng/ml KGF | 10ug/ml Heparin | |
| | | | | | 20ng/ml Betacellulin | |
| Small molecules | 3μM ChiR99021 Day 1 | | 2μM RA | 100nM RA | 50nM RA (1st 4 days, then 25nM) | 10μM AlkSi II |
| | | | 0.25μM SANT1 | 0.25μM SANT1 | 0.25μM SANT1 (1st 4 days) | 1μM T3 |
| | | | 100nM LDN (Day0) | | 10μM AlkSi II | |
| | | | 500nM PdBU | | 1μM T3 | |
| | | | | | 1μM XXI | |
| Step duration (days) | 3 | 3 | 2 | 3 | 7 | 14 |
| Media changes during each step | days 1,2 | days 1,3 | each day | every 2nd day | every 2nd day | every 2nd day |

SERUM-FREE IN VITRO DIRECTED DIFFERENTIATION PROTOCOL FOR GENERATING STEM CELL-DERIVED BETA CELLS AND USES THEREOF

RELATED APPLICATIONS

This application is a continuation application of U.S. application Ser. No. 16/573,985, filed Sep. 17, 2019, which is a continuation application of U.S. application Ser. No. 14/975,158, filed Dec. 18, 2015 (U.S. Pat. No. 10,443,042), which claims the benefit of U.S. Provisional Application Ser. No. 62/094,010, filed Dec. 18, 2014. The entire teachings of the above applications are incorporated herein by reference.

BACKGROUND OF THE INVENTION

Diabetes affects more than 300 million people worldwide according to the International Diabetes Federation. Type 1 diabetes and type 2 diabetes involve β cell destruction and/or δ cell dysfunction. Diabetic patients, particularly those suffering from type 1 diabetes, could potentially be cured through transplantation of β cells. While cadaveric human islet transplantation can render patients insulin independent for 5 years or longer, such approach is limited due to the scarcity and quality of donor islets (Bellin et al., 2012). Generating an unlimited supply of human β cells from stem cells could provide therapy to millions of patients as only a single cell type, the β cell, likely needs to be produced, and the mode of delivery is well understood: transplantation to a vascularized location within the body with immunoprotection. In addition, screening to identify novel drugs that improve β cell function, survival, or proliferation is also delayed due to limited islet supply and variability resulting from different causes of death, donor genetics, and other aspects in their isolation. As such, a steady, uniform supply of stem-cell-derived β cells would offer a useful drug discovery platform for diabetes. Moreover, genetically diverse stem-cell-derived β cells could be used for disease modeling in vitro or in vivo.

SUMMARY OF THE INVENTION

There is a need for methods of generating stem cell-derived β (SC-β) cells. The present invention is directed toward solutions to address this need, in addition to having other desirable characteristics.

In accordance with an embodiment of the present invention, a method of generating at least one SC-β cell is provided. The method includes differentiating at least one PDX1+, NKX6.1+, insulin+ endocrine cell in a population into at least one SC-β cell by treatment with a first chemically defined, serum free medium that is supplemented with at least i) a transforming growth factor β (TGF-β) signaling pathway inhibitor, ii) a thyroid hormone signaling pathway activator, iii) insulin, iv) heparin, and v) a water soluble antioxidant, thereby generating at least one SC-β cell that exhibits a GSIS response in vitro and/or in vivo.

In accordance with aspects of the present invention, the method includes washing the cells in the population with CMRLM before treatment with the first medium.

In accordance with aspects of the present invention, the first medium comprises CMRL 1066 with 2.2 g/L $NaHCO_3$, but without HEPES, 1% Pen/Strep, and 2 mM Glutamax. In accordance with aspects of the present invention, the first medium is supplemented with FAF-BSA, human APO-transferrin, trace minerals A+B, ZnSO4, ethanolamine, pyruvate, and defined lipids. In accordance with aspects of the present invention, the first medium is replenished every second day during a 14 day differentiation period. In accordance with aspects of the present invention, at least 25% of the cells in the population express PDX1, NKX6.1 and/or insulin before treatment with the first medium. In accordance with aspects of the present invention, between at least 25% and 75% of the PDX1+, NKX6.1+, insulin+ endocrine cells in the population differentiate into SC-β cells.

In accordance with aspects of the present invention, the at least one PDX1+, NKX6.1+, insulin-positive endocrine cell is obtained by differentiating at least one PDX1+, NKX6.1+ pancreatic progenitor cell in the population into at least one PDX1+, NKX6.1+, insulin-positive endocrine cell by treatment with a second chemically defined, serum free medium that is supplemented with at least i) heparin, ii) an EGF family growth factor, iii) a retinoic signaling pathway activator, iv) a sonic hedgehog pathway inhibitor, v) a BMP signaling pathway inhibitor, vi) a thyroid signaling pathway activator, vii) a γ-secretase inhibitor, viii) a protein kinase inhibitor, and a rho-associated protein kinase (ROCK) inhibitor.

In accordance with aspects of the present invention, the method includes washing the cells in the population with BE5 before treatment with the second medium. In accordance with aspects of the present invention, the second medium comprises MCDB131, 1% Pen/Strep, 1.75 g/L $NaHCO_3$ and 2 mM Glutamax. In accordance with aspects of the present invention, the second medium is supplemented with FAF-BSA, ITS-X, Glucose, $ZnSO_4$. In accordance with aspects of the present invention, the second medium is not supplemented with Vitamin C. In accordance with aspects of the present invention, the population of cells is treated with the second medium on day 1, day 2, day 4 and day 6 of a 7 day differentiation period, with the proviso that the sonic hedgehog pathway inhibitor is absent from the second medium on day 4, day 5, day 6 and day 7. In accordance with aspects of the present invention, at least 50% of the cells in the population express PDX1 and NKX6.1 before treatment with the second medium. In accordance with aspects of the present invention, between at least 25% and 75% of the PDX1+, NKX6.1+ pancreatic progenitor cells in the population differentiate into PDX1+, NKX6.1+, insulin+ endocrine cells.

In accordance with aspects of the present invention, the PDX1+, NKX6.1+ pancreatic progenitor cells are obtained by differentiating at least one PDX1+ pancreatic progenitor cell in the population into at least one PDX1+, NKX6.1+ pancreatic progenitor cells by treatment with a third chemically defined, serum free medium that is supplemented with at least i) a FGF family growth factor, ii) a TGFβ superfamily member, iii) a retinoic signaling pathway activator, iv) a sonic hedgehog pathway inhibitor, and v) a ROCK inhibitor.

In accordance with aspects of the present invention, the third medium comprises MCDB131, 1% Pen/Strep, 1.23 g/L $NaHCO_3$ and 2 mM Glutamax. In accordance with aspects of the present invention, the third medium is supplemented with FAF-BSA, ITS-X, Glucose, and Vitamin C. In accordance with aspects of the present invention, the third medium is replenished every second day during a 6 day differentiation period. In accordance with aspects of the present invention, at least 50% of the cells in the population express PDX1 before treatment with the third medium. In accordance with aspects of the present invention, between at least 25% and 75% of the PDX1+ pancreatic progenitor cells in the population differentiate into PDX1+, NKX6.1+ pancreatic progenitor cells.

In accordance with aspects of the present invention, the PDX1+ pancreatic progenitor cells are obtained by differentiating at least one FOXA2+, SOX2+ foregut endoderm cell in the population into at least one PDX1+ pancreatic progenitor cell by treatment with a fourth chemically defined, serum free medium that is supplemented with at least i) a FGF family growth factor, ii) a retinoic acid signaling activator, iii) a sonic hedgehog pathway inhibitor, iv) a BMP pathway signaling inhibitor, v) a protein kinase C (PKC) activator, and vi) a ROCK inhibitor.

In accordance with aspects of the present invention, the fourth medium comprises MCDB131, 1% Pen/Strep, 1.23 g/L NaHCO$_3$ and 2 mM Glutamax. In accordance with aspects of the present invention, the fourth medium is supplemented with FAF-BSA, ITS-X, Glucose, and Vitamin C. In accordance with aspects of the present invention, the fourth medium is replenished without the PKC activator on the second day of a 2 day differentiation period. In accordance with aspects of the present invention, at least 50% of the cells in the population express FOXA2 and/or SOX2 before treatment with the fourth medium. In accordance with aspects of the present invention, between at least 25% and 75% of the FOXA2+, SOX2+ foregut endoderm cells in the population differentiate into PDX1+ pancreatic progenitor cells.

In accordance with aspects of the present invention, the FOXA2+, SOX2+ foregut endoderm cells are obtained by differentiating at least one SOX17+ definitive endoderm cell in the population into at least one FOXA2+, SOX2+ foregut endoderm cell by treatment with a fifth chemically defined, serum free medium that is supplemented with at least i) a FGF family growth factor.

In accordance with aspects of the present invention, the fifth medium comprises MCDB131, 1% Pen/Strep, 1.23 g/L NaHCO$_3$ and 2 mM Glutamax. In accordance with aspects of the present invention, the fifth medium is supplemented with FAF-BSA, ITS-X, Glucose, and Vitamin C. In accordance with aspects of the present invention, the cells in the population are treated with the fifth medium on day 1 and day 3 of a 3 day differentiation period. In accordance with aspects of the present invention, at least 50% of the cells in the population express SOX17 before treatment with the fifth medium. In accordance with aspects of the present invention, between at least 25% and 75% of the SOX17+ definitive endoderm cells in the population differentiate into FOXA2+, SOX2+ foregut endoderm cells.

In accordance with aspects of the present invention, the FOXA2+, SOX2+ foregut endoderm cells are obtained by differentiating at least one pluripotent stem cell in the population into at least one SOX17+ definitive endoderm cell by treatment with a sixth chemically defined, serum free medium that is supplemented with at least i) a TGFβ superfamily member and ii) a WNT signaling pathway activator.

In accordance with aspects of the present invention, the sixth medium comprises MCDB131, 1% Pen/Strep, 2.5 g/L NaHCO$_3$ and 2 mM Glutamax. In accordance with aspects of the present invention, the sixth medium is supplemented with FAF-BSA, ITS-X, Glucose, and Vitamin C. In accordance with aspects of the present invention, the pluripotent stem cells are treated with the sixth medium on day 1 with the WNT signaling pathway activator and on day 2 without the WNT signaling pathway activator during a 3 day differentiation period. In accordance with aspects of the present invention, between at least 25% and 75% of the pluripotent stem cells in the population differentiate into SOX17+ definitive endoderm cells.

In accordance with an embodiment of the present invention, an isolated SC-β cell or population thereof that exhibits a glucose stimulated insulin secretion (GSIS) response both in vitro and in vivo is provided. In accordance with aspects of the present invention, the isolated SC-β cell or population thereof exhibits a stimulation index that is at least between 1.0 and 3.0. In accordance with aspects of the present invention, the isolated SC-β cell or population thereof produces between approximately 300 uIU and 4000 uIU per 30 minute incubation at a high glucose concentration.

In accordance with an embodiment of the present invention, a microcapsule comprising the isolated SC-β cell or population thereof encapsulated therein is provided.

In accordance with an embodiment of the present invention, a macroencapsulation device comprising the isolated SC-β cell or population thereof encapsulated therein is provided.

In accordance with an embodiment of the present invention, a cell line comprising isolated SC-β cells that stably express insulin is provided.

In accordance with an embodiment of the present invention, assays comprising the isolated SC-β cell, or population thereof, or the cell line are provided. The assays can be used for: i) identifying one or more candidate agents which promote or inhibit a β cell fate selected from the group consisting of β cell proliferation, β cell replication, β cell death, β cell function, β cell susceptibility to immune attack, and β cell susceptibility to dedifferentiation or differentiation; or ii) identifying one or more candidate agents which promote the differentiation of at least one insulin-positive endocrine cell or a precursor thereof into at least one SC-β cell.

In accordance with an embodiment of the present invention, a method for the treatment of a subject in need thereof is disclosed. The method includes administering to a subject in need thereof i) an isolated population of SC-β cells, ii) a microcapsule comprising SC-β cells encapsulated therein; and/or iii) a macroencapsulation device comprising the SC-β cells encapsulated therein. In accordance with an embodiment of the present invention, an isolated population of SC-β cells, a microcapsule comprising the isolated population of SC-β cells, and/or a macroencapsulation device comprising the isolated population of SC-β cells is used for administering to a subject in need thereof. In accordance with aspects of the invention, the subject has, or has an increased risk of developing diabetes or has, or has an increased risk of developing a metabolic disorder.

In accordance with an embodiment of the present invention, an artificial islet or pancreas comprising SC-β cells is provided.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact-.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE DRAWINGS

FIG. 2A is a schematic illustrating the six stages of differentiation of human pluripotent stem cells to SC-β cells. hPSC=human pluripotent stem cell, DE=definitive endoderm cell, GT=gut tube cell, PP1=pancreatic progenitor cell 1, PP2=pancreatic progenitor cell 2, EN=endocrine progenitor cell, SC-β=stem cell-derived β cells.

FIG. 2B is a schematic illustrating an overview of an exemplary six step undefined differentiation protocol for generating SC-β cells from pluripotent stem cells, as described further in Pagliuca et al. 2014 and PCT International Application No. PCT/US2014/041992 (the teachings of both of which are incorporated herein by reference in their entirety).

FIG. 3A is a table depicting a more detailed overview of the exemplary six step undefined differentiation protocol shown in FIG. 2B.

FIG. 3B is a table depicting a detailed overview of an exemplary completely serum-free, chemically defined six step differentiation protocol according to an embodiment of the present invention.

DETAILED DESCRIPTION OF THE INVENTION

Figure 1:
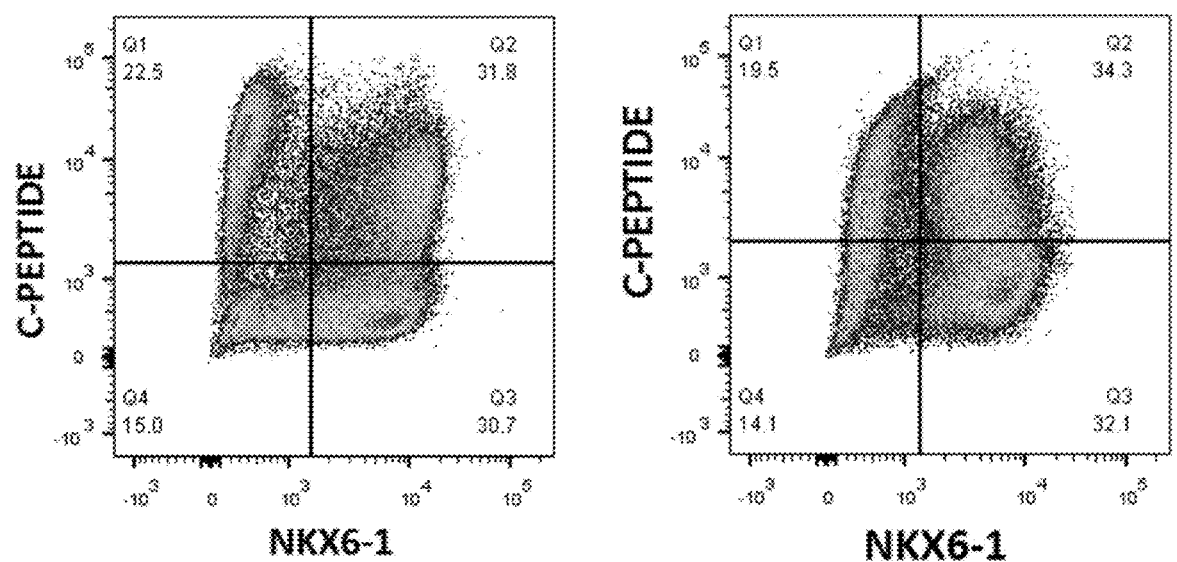
FIG. 1 shows a FACS plot of SC-β cells obtained at the end of Step 6 using an undefined medium in the exemplary 6 Step differentiation protocol shown in FIG. 2A (left panel) in a side-by-side comparison with a FACS plot of SC-β cells obtained at the end of Step 6 using a completely serum-free differentiation protocol according to an embodiment of the present invention (right panel), demonstrating that the completely serum-free differentiation protocol maintains marker expression at the end of Step 6.

The present invention is directed to a serum-free in vitro directed differentiation protocol for generating stem cell-derived β cells (SC-β cells), and uses of the SC-β cells generated by the protocol. More particularly, work described herein demonstrates that the completely serum-free, chemically defined six step in vitro differentiation protocol maintains marker expression at the end of the protocol despite the absence of serum in the cell culture medium throughout the protocol, as is shown in FIG. 1. The SC-β cells generated in accordance with the serum-free in vitro directed differentiation protocol of the present invention can be used in various assays to identify novel drugs that improve β cell function, survival, or proliferation, cell therapies (e.g., for treating diabetes and/or metabolic disorders), and in the construction of artificial islets and/or an artificial pancreas.

Some Definitions

"Differentiation" is the process by which an unspecialized ("uncommitted") or less specialized cell acquires the features of a specialized cell such as, for example, a pancreatic cell. A differentiated cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. As used herein, the lineage of a cell defines the heredity of the cell, i.e., which cells it came from and to what cells it can give rise. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

As used herein, "markers", are nucleic acid or polypeptide molecules that are differentially expressed in a cell of interest. Differential expression means an increased level for a positive marker and a decreased level for a negative marker as compared to an undifferentiated cell. The detectable level of the marker nucleic acid or polypeptide is sufficiently higher or lower in the cells of interest compared to other cells, such that the cell of interest can be identified and distinguished from other cells using any of a variety of methods known in the art.

As used herein, a cell is "positive" or "+" for a specific marker when the specific marker is sufficiently detected in the cell. Similarly, the cell is "negative" or "−" for a specific marker when the specific marker is not sufficiently detected in the cell. For example, positive by FACS is usually greater than 2%, whereas the negative threshold by FACS is usually less than 1%.

The process of differentiating pluripotent stem cells into functional pancreatic endocrine cells (i.e., SC-β cells) in vitro may be viewed as progressing through six consecutive stages, as is shown in the exemplary protocol depicted in FIG. 2A. In this step-wise progression, "Stage 1" or "S1" refers to the first step in the differentiation process, the differentiation of pluripotent stem cells into cells expressing markers characteristic of definitive endoderm cells ("DE", "Stage 1 cells" or "S1 cells"). "Stage 2" refers to the second step, the differentiation of cells expressing markers characteristic of definitive endoderm cells into cells expressing markers characteristic of gut tube cells ("GT", "Stage 2 cells" or "S2 cells"). "Stage 3" refers to the third step, the differentiation of cells expressing markers characteristic of gut tube cells into cells expressing markers characteristic of pancreatic progenitor 1 cells ("PP1", "Stage 3 cells" or "S3 cells"). "Stage 4" refers to the fourth step, the differentiation of cells expressing markers characteristic of pancreatic progenitor 1 cells into cells expressing markers characteristic of pancreatic progenitor 2 cells ("PP2", "Stage 4 cells" or "S4 cells"). "Stage 5" refers to the fifth step, the differentiation of cells expressing markers characteristic of pancreatic progenitor 2 cells into cells expressing markers characteristic of pancreatic endoderm cells and/or pancreatic endocrine progenitor cells ("EN", "Stage 5 cells" or "S5 cells"). "Stage 6" refers to the differentiation of cells expressing markers characteristic of pancreatic endocrine progenitor cells into cells expressing markers characteristic of pancreatic endocrine β cells ("SC-β cells", "Stage 6 cells" or "S6 cells"). It should be appreciated, however, that not all cells in a particular population progress through these stages at the same rate, i.e., some cells may have progressed less, or more, down the differentiation pathway than the majority of cells present in the population.

Characteristics of the various cell types associated with the stages shown in FIG. 2A are now described. "Definitive endoderm cells," as used herein, refers to cells which bear the characteristics of cells arising from the epiblast during gastrulation and which form the gastrointestinal tract and its derivatives. Definitive endoderm cells express at least one of the following markers: FOXA2 (also known as hepatocyte nuclear factor 3δ ("HNF3β")), GATA4, SOX17, CXCR4, Brachyury, Cerberus, OTX2, goosecoid, C-Kit, CD99, and MIXL1. Markers characteristic of the definitive endoderm cells include CXCR4, FOXA2 and SOX17. Thus, definitive endoderm cells may be characterized by their expression of CXCR4, FOXA2 and SOX17. In addition, depending on the length of time cells are allowed to remain in Stage 1, an increase in HNF4α may be observed.

"Gut tube cells," as used herein, refers to cells derived from definitive endoderm that can give rise to all endodermal organs, such as lungs, liver, pancreas, stomach, and intestine. Gut tube cells may be characterized by their substantially increased expression of HNF4α over that expressed by definitive endoderm cells. For example, a ten to forty fold increase in mRNA expression of HNF4α may be observed during Stage 2.

"Pancreatic progenitor 1 cells," as used herein, refers to endoderm cells that give rise to the esophagus, lungs, stomach, liver, pancreas, gall bladder, and a portion of the duodenum. Pancreatic progenitor 1 cells express at least one of the following markers: PDX1, FOXA2, CDX2, SOX2, and HNF4a. Pancreatic progenitor 1 cells may be characterized by an increase in expression of PDX1, compared to gut tube cells. For example, greater than fifty percent of the cells in Stage 3 cultures typically express PDX1.

"Pancreatic progenitor 2 cells," as used herein, refers to cells that express at least one of the following markers: PDX1, NKX6.1, HNF6, NGN3, SOX9, PAX4, PAX6, ISL1, gastrin, FOXA2, PTF1a, PROX1 and HNF4α. Pancreatic progenitor 2 cells may be characterized as positive for the expression of PDX1, NKX6.1, and SOX9.

"Pancreatic endocrine progenitor cells" or "endocrine progenitor cells" are used interchangeably herein to refer to pancreatic endoderm cells capable of becoming a pancreatic hormone expressing cell. Pancreatic endocrine progenitor cells express at least one of the following markers: NGN3; NKX2.2; NeuroD1; ISL1; PAX4; PAX6; or ARX. Pancreatic endocrine progenitor cells may be characterized by their expression of NKX2.2 and NeuroD1.

A "precursor thereof" as the term relates to a pancreatic endocrine progenitor cell refers to any cell that is capable of differentiating into a pancreatic endocrine progenitor cell, including for example, a pluripotent stem cell, a definitive endoderm cell, a gut tube cell, or a pancreatic progenitor cell, when cultured under conditions suitable for differentiating the precursor cell into the pancreatic pro endocrine cell.

"Pancreatic endocrine cells," as used herein, refer to cells capable of expressing at least one of the following hormones: insulin, glucagon, somatostatin, ghrelin, and pancreatic polypeptide. In addition to these hormones, markers characteristic of pancreatic endocrine cells include one or more of NGN3, NeuroD1, ISL1, PDX1, NKX6.1, PAX4, ARX, NKX2.2, and PAX6. Pancreatic endocrine cells expressing markers characteristic of β cells can be characterized by their expression of insulin and at least one of the following transcription factors: PDX1, NKX2.2, NKX6.1, NeuroD1, ISL1, HNF3O, MAFA and PAX6.

The terms "stem cell-derived β cell" and "SC-β cell" are used interchangeably herein to refer to cells differentiated in vitro (e.g., from pluripotent stem cells) that display at least one marker indicative of a pancreatic β cell (e.g., PDX-1 or NKX6-1), expresses insulin, and display a GSIS response characteristic of an endogenous mature β cell both in vitro and in vivo. The GSIS response of the SC-β cells can be observed within two weeks of transplantation of the SC-β cell into a host (e.g., a human or animal). It is to be understood that the SC-β cells need not be derived (e.g., directly) from stem cells, as the methods of the disclosure are capable of deriving SC-β cells from any endocrine progenitor cell that expresses insulin or precursor thereof using any cell as a starting point (e.g., one can use embryonic stem cells, induced-pluripotent stem cells, progenitor cells, partially reprogrammed somatic cells (e.g., a somatic cell which has been partially reprogrammed to an intermediate state between an induced pluripotent stem cell and the somatic cell from which it was derived), multipotent cells, totipotent cells, a transdifferentiated version of any of the foregoing cells, etc, as the invention is not intended to be limited in this manner). In some aspects, human cells are excluded that are derived from human embryonic stem cells obtained exclusively by a method necessitating the destruction of an embryo. The skilled artisan is well aware of such methods and how to avoid them for the purposes of generating SC-β cells according to the methods of the present invention.

Used interchangeably herein are "d1", "1d", and "day 1"; "d2", "2d", and "day 2", etc. These number letter combinations refer to a specific day of incubation in the different stages during the stepwise differentiation protocol of the instant application.

Methods for Generating SC-β Cells

Recently, two protocols for directing the differentiation of pluripotent stem cells in vitro into insulin-producing endocrine cells that express key markers of mature pancreatic β cells (e.g., SC-β cells) have been reported, each of which includes differentiating cells into endocrine progenitor cells that can be directed to differentiate into SC-β cells, as well as protocols for directing the pancreatic endocrine progenitor cells into SC-β cells, which can be used in the method disclosed herein for generating SC-β cells. First, as is shown in FIG. 2B, a six-stage protocol for the large-scale production of functional human β cells using human pluripotent stem cells (hPSC) by sequential modulation of multiple signaling pathways in a three-dimensional cell culture system using chemically undefined medium, without using any transgenes or genetic modification, was used to generate glucose-responsive, monohormonal insulin-producing cells that exhibited key β cell markers and β cell ultrastructure (see Pagliuca et al., 2014 and PCT International Application No. PCT/US2014/041992, both of which are incorporated herein by reference in their entirety). FIG. 3A shows a more detailed overview of the exemplary six-stage protocol shown in FIG. 2B. Pagliuca and colleagues reported that such cells mimicked the function of human islets in vitro and in vivo, and demonstrated the potential utility of such cells for in vivo transplantation to treat diabetes. Secondly, a seven-stage protocol that converts human embryonic stem cells (hESCs) into insulin-producing cells that expressed key markers of mature pancreatic β cells, such as MAFA, and displayed glucose-stimulated insulin secretion like that of human islets using static incubations in vitro was described (Rezania et al., 2014). Cells produced by such protocol, referred to as S7 cells, were found to rapidly reverse diabetics in mice within a little over a month.

Figure 3B:
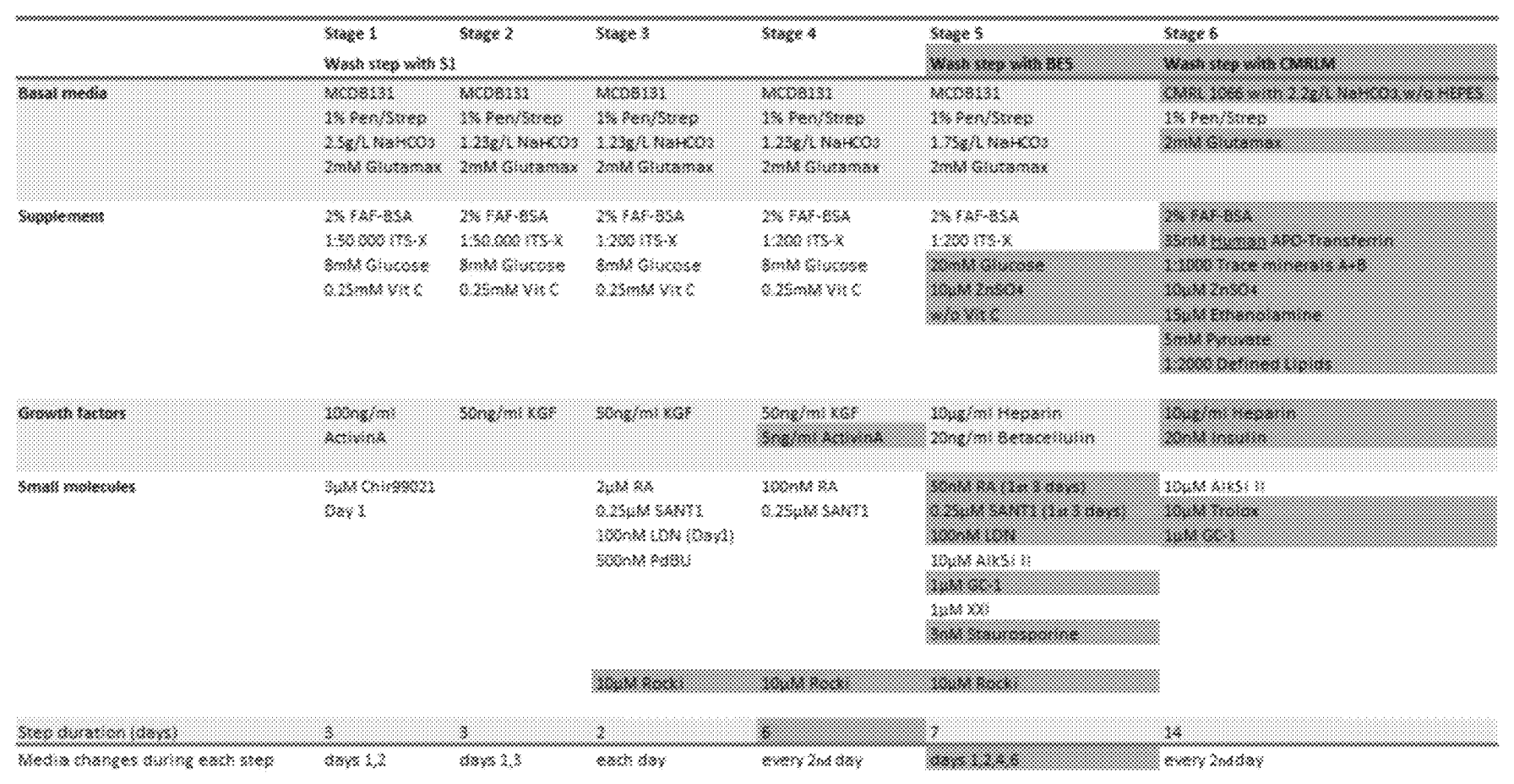

Completely Serum-Free, Chemically Defined Six Step In Vitro Directed Differentiation Protocol for Generating SC-β Cells FIG. 3B shows an exemplary completely serum-free, chemically defined six step in vitro directed differentiation protocol for generating SC-β cells in accordance with an embodiment of the present invention that produces SC-β cells that maintain marker expression at the end of the protocol.

The protocol of the present invention encompasses differentiating cells at all stages toward Stage 6. It should be appreciated, moreover, that although the process is described in discrete stages, the treatment, as well as the progress of cells through the process of differentiation, can be sequential or continuous. What follows is a description of exemplary embodiments of each of the six different stages of the completely serum-free in vitro directed differentiation protocol in reverse order, beginning with Stage 6.

Stage 6

In accordance with an embodiment of the present invention, a method for generating SC-β cells comprises differentiating at least one PDX1+, NKX6.1+, insulin+ endocrine cells in a population into SC-β cells by treatment with a first chemically defined, serum free medium that is supplemented with at least i) a transforming growth factor β (TGF-β) signaling pathway inhibitor, ii) a thyroid hormone signaling pathway activator, thereby generating SC-β cells that exhibit a GSIS response in vitro and/or in vivo. The terms "first chemically defined, serum free medium" and "first medium" are used interchangeably herein. As used herein, the term "X positive" or "X+" means expressing X.

Washing Step

In accordance with aspects of the invention, the method includes washing the cells in the population with CMRLM before treatment with the first chemically defined, serum free medium.

First Chemically Defined, Serum Free Medium (First Medium)

The present invention contemplates any chemically defined, serum free medium that contributes to the induction of PDX1+, NKX6.1+, insulin+ endocrine cells to differentiate and/or mature into SC-β cells. In accordance with aspects of the present invention, the first medium comprises CMRL 1066 with 2.2 g/L NaHCO$_3$, but without HEPES, 1% Pen/Strep, and 2 mM Glutamax.

In accordance with aspects of the present invention, the first medium is supplemented with one or more agents selected from the group consisting of FAF-BSA, human APO-transferrin, trace minerals A+B, ZnSO$_4$, ethanolamine, pyruvate, and defined lipids. In accordance with aspects of the present invention, the first medium is supplemented with 2% FAF-BSA, 35 nM human APO-transferrin, 1:1000 trace minerals A+B, 10 μM ZnSO$_4$, 15 μM ethanolamine, 5 mM pyruvate, and 1:2000 defined lipids.

The first medium may be changed at any time throughout differentiation stage 6 (e.g., day 1, day 2, day 3, day 4, day 5, day 6, day 7, day 8, day 9, day 10, day 11, day 12, day 13, day 14, day 15, day 16, day 17, day 18, day 19, day 20, day 21, etc.). In accordance with aspects of the present invention, the first medium is replenished every second day during a 14 day differentiation period.

In accordance with aspects of the present invention, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, at least 80%, at least 85%, at least 90%, or at least 95% or greater of the cells in the population comprise PDX1+, NKX6.1+, insulin+ endocrine progenitor cells expressing PDX1, NKX6.1, and/or insulin before treatment with the first medium.

In accordance with aspects of the present invention, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, at least 80%, at least 85%, at least 90%, or at least 95% or greater of the PDX1+, NKX6.1+, insulin+ endocrine cells in the population differentiate into SC-β cells after treatment with the first medium.

The PDX1+, NKX6.1+, insulin+ endocrine cells in the population treated with the first medium can be obtained by differentiating at least one PDX1+, NKX6.1+ pancreatic progenitor cell in the population into at least one PDX1+, NKX6.1+, insulin-positive endocrine cell, and optionally isolating, expanding, purifying, and/or washing the population of PDX1+, NKX6.1+, insulin-positive endocrine cells before treatment with the first medium.

Stage 5

The present invention contemplates differentiating PDX1+, NKX6.1+ pancreatic progenitor cells (PP2, or S4 cells) into PDX1+, NKX6.1+, insulin-positive endocrine cells (EN, or S5 cells) in chemically defined, completely serum-free conditions, and subsequently differentiating the PDX1+, NKX6.1+, insulin-positive endocrine cells into SC-β cells under chemically defined, completely serum-free conditions.

In accordance with an embodiment of the present invention, a method for generating an SC-β cell comprises: a) differentiating at least one PDX1+, NKX6.1+ pancreatic progenitor cells in the population into PDX1+, NKX6.1+, insulin-positive endocrine cells by treatment with a second chemically defined, serum free medium that is supplemented with at least i) heparin, ii) an EGF family growth factor, iii) a retinoic signaling pathway activator, iv) a sonic hedgehog pathway inhibitor, v) a BMP signaling pathway inhibitor, vi) a thyroid signaling pathway activator, vii) a γ-secretase inhibitor, viii) a protein kinase inhibitor, and a rho-associated protein kinase (ROCK) inhibitor; and b) differentiating at least one PDX1+, NKX6.1+, insulin-positive endocrine cell in the population into at least one SC-β cell, thereby generating an SC-β cell; e.g., by treatment of the at least one PDX1+, NKX6.1+, insulin-positive endocrine cell with the first medium.

In accordance with an aspect of the present invention, the PDX1+, NKX6.1+, insulin-positive endocrine cells are obtained by differentiating at least one PDX1+, NKX6.1+ pancreatic progenitor cells in the population into PDX1+, NKX6.1+, insulin-positive endocrine cells by treatment with a second chemically defined, serum free medium that is supplemented with at least i) heparin, ii) an EGF family growth factor, iii) a retinoic signaling pathway activator, iv) a sonic hedgehog pathway inhibitor, v) a BMP signaling pathway inhibitor, vi) a thyroid signaling pathway activator, vii) a γ-secretase inhibitor, viii) a protein kinase inhibitor, and a rho-associated protein kinase (ROCK) inhibitor.

In accordance with aspects of the present invention, the method includes washing the cells in the population with BE5 before treatment with the second chemically defined, serum free medium. In accordance with aspects of the present invention, BE5 comprises MCDB131+20 mM D-Glucose+1.754 g/L NaHCO$_3$+2% FAF-BSA+ITS-X 1:200+2 mM Glutamax+0.25 mM Vitamin C+1% Pen/Strep+Heparin 10 μg/ml (Sigma; H3149).

Second Chemically Defined, Serum Free Medium (Second Medium)

The present invention contemplates any chemically defined, serum free medium that contributes to the induction of PDX1+, NKX6.1+ pancreatic progenitor cells to differentiate into PDX1+, NKX6.1+, insulin-positive endocrine cells. In accordance with aspects of the present invention, the second medium comprises MCDB131, 1% Pen/Strep, 1.75 g/L NaHCO$_3$ and 2 mM Glutamax.

In accordance with aspects of the present invention, the second medium is supplemented with one or more agents selected from the group consisting of FAF-BSA, ITS-X, Glucose, ZnSO$_4$. In accordance with aspects of the present invention, the second medium is supplemented with 2% FAF-BSA, 1:200 ITS-X, 20 mM Glucose, and 10 μM ZnSO$_4$. In accordance with aspects of the present invention, the second chemically defined, serum free medium is not supplemented with Vitamin C.

The second medium may be changed at any time throughout differentiation stage 5 (e.g., day 1, day 2, day 3, day 4, day 5, day 6, day 7, day 8, day 9, day 10, day 11, day 12, day 13, day 14, etc.). In accordance with aspects of the present invention, the population of cells is treated with the second medium on day 1, day 2, day 4 and day 6 of a 7 day differentiation period, with the proviso that the sonic hedgehog pathway inhibitor is absent from the second chemically defined, serum free medium on day 4, day 5, day 6 and day 7.

In accordance with aspects of the present invention, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, at least 80%, at least 85%, at least 90%, or at least 95% or greater of the cells in the population comprise PDX1+, NKX6.1+ pancreatic progenitor cells expressing PDX1 and NKX6.1 before treatment with the second medium.

In accordance with aspects of the present invention, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, at least 80%, at least 85%, at least 90%, or at least 95% or greater of the PDX1+, NKX6.1+ pancreatic progenitor cells in the population differentiate into PDX1+, NKX6.1+, insulin+ endocrine cells after treatment with the second medium.

The PDX1+, NKX6.1+ pancreatic progenitor cells in the population treated with the second medium can be obtained by differentiating at least one PDX1+ pancreatic progenitor cell in the population into at least one PDX1+, NKX6.1+ pancreatic progenitor cell, and optionally isolating, expanding, purifying, and/or washing the PDX1+, NKX6.1+ pancreatic progenitor cells before treatment with the second medium.

Stage 4

The present invention contemplates differentiating PDX1+ pancreatic progenitor cells (PP1, or S3 cells) into PDX1+, NKX6.1+ pancreatic progenitor cells (PP2, or S4 cells) in chemically defined, completely serum-free conditions, and subsequently differentiating the PDX1+, NKX6.1+ pancreatic progenitor cells into PDX1+, NKX6.1+, insulin-positive endocrine cells, and/or into SC-β cells under chemically defined, completely serum-free conditions.

In accordance with an embodiment of the present invention, a method for generating an SC-β cell comprises: a) differentiating at least one PDX1+ pancreatic progenitor cell in the population into PDX1+, NKX6.1+ pancreatic progenitor cells by treatment with a third chemically defined, serum free medium that is supplemented with at least i) a FGF family growth factor, ii) a TGFβ superfamily member, iii) a retinoic signaling pathway activator, iv) a sonic hedgehog pathway inhibitor, and v) a ROCK inhibitor; b) differentiating the at least one PDX1+, NKX6.1+ pancreatic progenitor cell in the population to at least one PDX1+, NKX6.1+, insulin+ endocrine cell, e.g., by treatment with the second medium; and c) differentiating the at least one PDX1+, NKX6.1+, insulin+ endocrine cell in the population to at least one SC-β cell, e.g., by treatment with the first medium, thereby generating an SC-β cell.

In accordance with aspects of the present invention, the PDX1+, NKX6.1+ pancreatic progenitor cells are obtained by differentiating at least one PDX1+ pancreatic progenitor cell in the population into at least one PDX1+, NKX6.1+ pancreatic progenitor cell by treatment with a third chemically defined, serum free medium that is supplemented with at least i) a FGF family growth factor, ii) a TGFβ superfamily member, iii) a retinoic signaling pathway activator, iv) a sonic hedgehog pathway inhibitor, and v) a ROCK inhibitor.

Third Chemically Defined, Serum Free Medium (Third Medium)

The present invention contemplates any chemically defined, serum free medium that contributes to the induction of PDX1+ pancreatic progenitor cells to differentiate into PDX1+, NKX6.1+ pancreatic progenitor cells. In accordance with aspects of the present invention, the third medium comprises MCDB131, 1% Pen/Strep, 1.23 g/L NaHCO$_3$ and 2 mM Glutamax.

In accordance with aspects of the present invention, the third medium is supplemented with one or more agents selected from the group consisting of FAF-BSA, ITS-X, Glucose, and Vitamin C. In accordance with aspects of the present invention, the third medium is supplemented with 2% FAF-BSA, 1:200 ITS-X, 8 mM Glucose, and 0.25 mM Vitamin C.

The third medium may be changed at any time throughout differentiation stage 4 (e.g., day 1, day 2, day 3, day 4, day 5, day 6, day 7, day 8, day 9, day 10, day 11, day 12, day 13, day 14, etc.). In accordance with aspects of the present invention, the third medium is replenished every second day during a 6 day differentiation period.

In accordance with aspects of the present invention, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, at least 80%, at least 85%, at least 90%, or at least 95% or greater of the cells in the population comprise PDX1+ pancreatic progenitor cells expressing PDX1+ before treatment with the third medium.

In accordance with aspects of the present invention, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, at least 80%, at least 85%, at least 90%, or at least 95% or greater of the PDX1+ pancreatic progenitor cells in the population differentiate into PDX1+, NKX6.1+ pancreatic progenitor cells after treatment with the third medium.

The PDX1+ pancreatic progenitor cells in the population treated with the third medium can be obtained by differentiating at least one FOXA2+, SOX2+ foregut endoderm cell in the population into at least one PDX1+ pancreatic progenitor cell, and optionally isolating, expanding, purifying, and/or washing the PDX1+ pancreatic progenitor cell before treatment with the third medium.

Stage 3

The present invention contemplates differentiating FOXA2+, SOX2+ foregut endoderm cells (GT, or S2 cells) into PDX1+(PP1, or S3 cells) in chemically defined, completely serum-free conditions, and subsequently differentiating the PDX1+ pancreatic progenitor cells into PDX1+, NKX6.1+ pancreatic progenitor cells, PDX1+, NKX6.1+, insulin-positive endocrine cells, and/or into SC-β cells under chemically defined, completely serum-free conditions.

In accordance with an embodiment of the present invention, a method for generating an SC-β cell comprises: a) differentiating at least one FOXA2+, SOX2+ foregut endoderm cell in the population into at least one PDX1+ pancreatic progenitor cell by treatment with a fourth chemically defined, serum free medium that is supplemented with at least i) a FGF family growth factor, ii) a retinoic acid signaling activator, iii) a sonic hedgehog pathway inhibitor, iv) a BMP pathway signaling inhibitor, v) a protein kinase C (PKC) activator, and vi) a ROCK inhibitor; b) differentiating the at least one PDX1+ pancreatic progenitor cell in the population into at least one PDX1+, NKX6.1+ pancreatic progenitor cell e.g., by treatment with the third medium; c) differentiating the at least one PDX1+, NKX6.1+ pancreatic progenitor cell in the population to at least one PDX1+, NKX6.1+, insulin+ endocrine cell, e.g., by treatment with the second medium; and d) differentiating the at least one PDX1+, NKX6.1+, insulin+ endocrine cell in the population to at least one SC-β cell, e.g., by treatment with the first medium, thereby generating an SC-β cell.

In accordance with aspects of the present invention, the PDX1+ pancreatic progenitor cells are obtained by differentiating at least one FOXA2+, SOX2+ foregut endoderm cells in the population into PDX1+ pancreatic progenitor cells by treatment with a fourth chemically defined, serum free medium that is supplemented with at least i) a FGF family growth factor, ii) a retinoic acid signaling activator, iii) a sonic hedgehog pathway inhibitor, iv) a BMP pathway signaling inhibitor, v) a protein kinase C (PKC) activator, and vi) a ROCK inhibitor.

Fourth Chemically Defined, Serum Free Medium (Fourth Medium)

The present invention contemplates any chemically defined, serum free medium that contributes to the induction of FOXA2+, SOX2+ foregut endoderm cells to differentiate into PDX1+ pancreatic progenitor cells. In accordance with aspects of the present invention, the fourth medium comprises MCDB131, 1% Pen/Strep, 1.23 g/L NaHCO$_3$ and 2 mM Glutamax.

In accordance with aspects of the present invention, the fourth medium is supplemented with one or more agents selected from the group consisting of FAF-BSA, ITS-X, Glucose, and Vitamin C. In accordance with aspects of the present invention, the fourth medium is supplemented with 2% FAF-BSA, 1:200 ITS-X, 8 mM Glucose, and 0.25 mM Vitamin C.

The fourth medium may be changed at any time throughout differentiation stage 3 (e.g., day 1, day 2, day 3, day 4, day 5, day 6, day 7, etc.). In accordance with aspects of the present invention, the fourth medium is replenished without the PKC activator on the second day of a 2 day differentiation period.

In accordance with aspects of the present invention, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, at least 80%, at least 85%, at least 90%, or at least 95% or greater of the cells in the population comprise FOXA2+, SOX2+ foregut endoderm cells expressing FOXA2 and/or SOX2 before treatment with the fourth medium.

In accordance with aspects of the present invention, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, at least 80%, at least 85%, at least 90%, or at least 95% or greater of the FOXA2+, SOX2+ foregut endoderm cells in the population differentiate into PDX1+ pancreatic progenitor cells after treatment with the fourth medium.

The FOXA2+, SOX2+ foregut endoderm cells in the population treated with the fourth medium can be obtained by differentiating at least one SOX17+ definitive endoderm cell in the population into at least one FOXA2+, SOX2+ foregut endoderm cell, and optionally isolating, expanding, purifying, and/or washing the FOXA2+, SOX2+ foregut endoderm cell before treatment with the fourth medium.

Stage 2

The present invention contemplates differentiating SOX17+ definitive endoderm cells (DE, or S1 cells) into FOXA2+, SOX2+ foregut endoderm cells (GT, or S2 cells) in chemically defined, completely serum-free conditions, and subsequently differentiating the FOXA2+, SOX2+ foregut endoderm cells into PDX1+ pancreatic progenitor cells, PDX1+, NKX6.1+ pancreatic progenitor cells, PDX1+, NKX6.1+, insulin-positive endocrine cells, and/or into SC-β cells under chemically defined, completely serum-free conditions.

In accordance with an embodiment of the present invention, a method for generating an SC-β cell comprises: a) differentiating at least one SOX17+ definitive endoderm cell in the population into at least one FOXA2+, SOX2+ foregut endoderm cell by treatment with a fifth chemically defined, serum free medium that is supplemented with at least i) a FGF family growth factor; b) differentiating the at least one FOXA2+, SOX2+ foregut endoderm cell in the population into at least one PDX1+ pancreatic progenitor cell e.g., by treatment with the fourth medium; c) differentiating the at least one PDX1+ pancreatic progenitor cell in the population into at least one PDX1+, NKX6.1+ pancreatic progenitor cell e.g., by treatment with the third medium; d) differentiating the at least one PDX1+, NKX6.1+ pancreatic progenitor cell in the population to at least one PDX1+, NKX6.1+, insulin+ endocrine cell, e.g., by treatment with the second medium; and e) differentiating the at least one PDX1+, NKX6.1+, insulin+ endocrine cell in the population to at least one SC-β cell, e.g., by treatment with the first medium, thereby generating an SC-β cell.

In accordance with aspects of the present invention, the FOXA2+, SOX2+ foregut endoderm cells are obtained by differentiating at least one SOX17+ definitive endoderm cells in the population into FOXA2+, SOX2+ foregut endoderm cells by treatment with a fifth chemically defined, serum free medium that is supplemented with at least i) a FGF family growth factor.

Fifth Chemically Defined, Serum Free Medium (Fifth Medium)

The present invention contemplates any chemically defined, serum free medium that contributes to the induction of SOX17+ definitive endoderm cells to differentiate into FOXA2+, SOX2+ foregut endoderm cells. In accordance with aspects of the present invention, the fifth medium comprises MCDB131, 1% Pen/Strep, 1.23 g/L NaHCO$_3$ and 2 mM Glutamax.

In accordance with aspects of the present invention, the fifth medium is supplemented with one or more agents selected from the group consisting of FAF-BSA, ITS-X, Glucose, and Vitamin C. In accordance with aspects of the present invention, the fifth medium is supplemented with 2% FAF-BSA, 1:50.000 ITS-X, 8 mM Glucose, and 0.25 mM Vitamin C.

The fifth medium may be changed at any time throughout differentiation stage 2 (e.g., day 1, day 2, day 3, day 4, day 5, day 6, day 7, etc.). In accordance with aspects of the present invention, the cells in the population are treated with the fifth medium on day 1 and day 3 of a 3 day differentiation period.

In accordance with aspects of the present invention, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, at least 80%, at least 85%, at least 90%, or at least 95% or greater of the cells in the population comprise SOX17+ definitive endoderm cells expressing SOX17 before treatment with the fifth medium.

In accordance with aspects of the present invention, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, at least 80%, at least 85%, at least 90%, or at least 95% or greater of the FOXA2+, SOX2+ foregut endoderm cells in the population differentiate into PDX1+ pancreatic progenitor cells after treatment with the fifth medium.

The SOX17+ definitive endoderm cells in the population treated with the fifth medium can be obtained by differentiating at least one pluripotent stem cell in the population into at least one SOX17+ definitive endoderm cell, and optionally isolating, expanding, purifying, and/or washing the SOX17+ definitive endoderm cell before treatment with the fifth medium.

Stage 1

The present invention contemplates differentiating pluripotent stem cells into SOX17+ definitive endoderm cells (DE, or S1 cells) in chemically defined, completely serum-free conditions, and subsequently differentiating the SOX17+ definitive endoderm cells into FOXA2+, SOX2+ foregut endoderm cells, PDX1+ pancreatic progenitor cells, PDX1+, NKX6.1+ pancreatic progenitor cells, PDX1+, NKX6.1+, insulin-positive endocrine cells, and/or into SC-β cells under chemically defined, completely serum-free conditions.

In accordance with an embodiment of the present invention, a method for generating an SC-β cell comprises: a) differentiating at least one pluripotent stem cell in the population into at least one SOX17+ definitive endoderm cell by treatment with a sixth chemically defined, serum free medium that is supplemented with at least i) a TGFβ superfamily member and ii) a WNT signaling pathway activator; b) differentiating at least one SOX17+ definitive endoderm cell in the population into at least one FOXA2+, SOX2+ foregut endoderm cell e.g., by treatment with the fifth medium; c) differentiating the at least one FOXA2+, SOX2+ foregut endoderm cell in the population into at least one PDX1+ pancreatic progenitor cell e.g., by treatment with the fourth medium; d) differentiating the at least one PDX1+ pancreatic progenitor cell in the population into at least one PDX1+, NKX6.1+ pancreatic progenitor cell e.g., by treatment with the third medium; e) differentiating the at least one PDX1+, NKX6.1+ pancreatic progenitor cell in the population to at least one PDX1+, NKX6.1+, insulin+ endocrine cell, e.g., by treatment with the second medium; and f) differentiating the at least one PDX1+, NKX6.1+, insulin+ endocrine cell in the population to at least one SC-β cell, e.g., by treatment with the first medium, thereby generating an SC-β cell.

In accordance with aspects of the present invention, the SOX17+ definitive endoderm cells are obtained by differentiating at least one pluripotent stem cell in the population into SOX17+ definitive endoderm cells by treatment with a sixth chemically defined, serum free medium that is supplemented with at least i) a TGFβ superfamily member and ii) a WNT signaling pathway activator.

Sixth Chemically Defined, Serum Free Medium (Sixth Medium)

The present invention contemplates any chemically defined, serum free medium that contributes to the induction of pluripotent stem cells S to differentiate into OX17+ definitive endoderm cells. In accordance with aspects of the present invention, the sixth medium comprises MCDB131, 1% Pen/Strep, 2.5 g/L NaHCO$_3$ and 2 mM Glutamax.

In accordance with aspects of the present invention, the sixth medium is supplemented with one or more agents selected from the group consisting of FAF-BSA, ITS-X, Glucose, and Vitamin C. In accordance with aspects of the present invention, the sixth medium is supplemented with 2% FAF-BSA, 1:50.000 ITS-X, 8 mM Glucose, and 0.25 mM Vitamin C.

The sixth medium may be changed at any time throughout differentiation stage 1 (e.g., day 1, day 2, day 3, day 4, day 5, day 6, day 7, etc.). In accordance with aspects of the present invention, the pluripotent stem cells are treated with the sixth medium on the day 1 with the WNT signaling pathway activator and on day 2 without the WNT signaling pathway activator during a 3 day differentiation period.

In accordance with aspects of the present invention, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, at least 80%, at least 85%, at least 90%, or at least 95% or greater of the pluripotent stem cells in the population differentiate into SOX17+ definitive endoderm cells after treatment with the sixth medium.

Agents Used in the Protocol

The present invention contemplates using "effective amounts" of agents in the protocol. As used herein, an "effective amount" of an agent when used in the first medium refers to the amount of the agent that should be present in the first medium for the differentiation of at least one PDX1+, NKX6.1+, insulin+ endocrine cell in the population into at least one SC-β cell. As used herein, an "effective amount" of an agent when used in the second medium refers to the amount that should be present in the second medium for the differentiation of at least one PDX1+, NKX6.1+ pancreatic progenitor cell into at least one PDX1+, NKX6.1+, insulin+ endocrine cell. As used herein, an "effective amount" of an agent when used in the third medium refers to the amount that should be present in the third medium for the differentiation of at least one PDX1+ pancreatic progenitor cell into at least one PDX1+, NKX6.1+ pancreatic progenitor cell. As used herein, an "effective amount" of an agent when used in the fourth medium refers to the amount that should be present in the fourth medium for the differentiation of at least one FOXA2+, SOX2+ foregut endoderm cell into at least one PDX1+ pancreatic progenitor cell. As used herein, an "effective amount" of an agent when used in the fifth medium refers to the amount that should be present in the fifth medium for the differentiation of at least one SOX17+ definitive endoderm cell into at least one FOXA2+, SOX2+ foregut endoderm cell. As used herein, an "effective amount" of an agent when used in the sixth medium refers to the amount that should be present in the sixth medium for the differentiation of at least one pluripotent stem cell (e.g., ESC, iPSC, etc.) into at least one SOX17+ definitive endoderm cell.

TGF-β Signaling Pathway Inhibitor

The first medium and/or the second medium may be supplemented with effective amounts of a TGF-β signaling pathway inhibitor. Exemplary TGF-β signaling pathway inhibitors include, without limitation, ALK5 inhibitor II (CAS 446859-33-2, an ATP-competitive inhibitor of TGF-B RI kinase, also known as RepSox, IUPAC Name: 2-[5-(6-methylpyridin-2-yl)-1H-pyrazol-4-yl]-1,5-naphthyridine, an analog or derivative of ALK5 inhibitor II, such as an analog or derivative of ALK5 inhibitor II of Formula I as described in U.S. Pub. No. 2012/0021519, a TGF-β receptor inhibitor described in U.S. Pub. No. 2010/0267731, an ALK5 inhibitor described in U.S. Pub Nos. 2009/0186076 and 2007/0142376, A 83-01, 431542, D 4476, GW 788388, LY 364947, LY 580276, SB 525334, SB 505124, SD 208, GW 6604, and GW 788388. It should be appreciated that any one of the above-mentioned TGF-β signaling pathway inhibitors can be excluded from the first chemically defined, serum free medium in accordance with aspects of the present invention. In accordance with aspects of the present invention, the TGF-β signaling pathway inhibitor comprises Alk5 inhibitor II.

An effective amount of the TGF-β signaling pathway inhibitor for use in the first medium and/or the second medium is from about 0.1 μM to about 110 μM. In accordance with aspects of the present invention, the first medium and/or the second medium is supplemented with about 0.1 μM to about 110 μM of Alk5 inhibitor II. In accordance with aspects of the present invention, the first medium and/or second medium is supplemented with about 10 μM of Alk5 inhibitor II.

Thyroid Hormone Signaling Pathway Activator

The first medium and/or the second medium may be supplemented with effective amounts of a thyroid hormone signaling pathway activator. Exemplary thyroid hormone signaling pathway activators include, without limitation, triiodothyronine (T3), an analog or derivative of T3, for example, selective and non-selective thyromimetics, TRβ selective agonist-GC-1, GC-24,4-Hydroxy-PCB 106, MB07811, MB07344,3,5-diiodothyropropionic acid (DITPA); the selective TR-β agonist GC-1; 3-Iodothyronamine (T(1)AM) and 3,3',5-triiodothyroacetic acid (Triac) (bioactive metabolites of the hormone thyroxine (T(4)); KB-2115 and KB-141; thyronamines; SKF L-94901; DIBIT; 3'-AC-T2; tetraiodothyroacetic acid (Tetrac) and triiodothyroacetic acid (Triac) (via oxidative deamination and decarboxylation of thyroxine [T4] and triiodothyronine [T3] alanine chain), 3,3',5'-triiodothyronine (rT3) (via T4 and T3 deiodination), 3,3'-diiodothyronine (3,3'-T2) and 3,5-diiodothyronine (T2) (via T4, T3, and rT3 deiodination), and 3-iodothyronamine (T1AM) and thyronamine (T0AM) (via T4 and T3 deiodination and amino acid decarboxylation), as well as for TH structural analogs, such as 3,5,3'-triiodothyropropionic acid (Triprop), 3,5-dibromo-3-pyridazinone-1-thyronine (L-940901), N-[3,5-dimethyl-4-(4'-hydroxy-3'-isopropylphenoxy)-phenyl]-oxamic acid (CGS 23425), 3,5-dimethyl-4-[(4'-hydroxy-3'-isopropylbenzyl)-phenoxy] acetic acid (GC-1), 3,5-dichloro-4-[(4-hydroxy-3-isopropylphenoxy)phenyl]acetic acid (KB-141), and 3,5-diiodothyropropionic acid (DITPA). In accordance with aspects of the present invention, the thyroid hormone signaling pathway activator comprises a prodrug or prohormone of T3, such as T4 thyroid hormone (e.g., thyroxine or L-3,5,3',5'-tetraiodothyronine). In accordance with aspects of the present invention, the thyroid hormone signaling pathway activator is an iodothyronine composition described in U.S. Pat. No. 7,163,918. In accordance with aspects of the present invention, the thyroid hormone signaling pathway activator is 2-[4-[[4-Hydroxy-3-(1-methylethyl)phenyl]methyl]-3,5-dimethylphenoxy]acetic acid (GC-1).

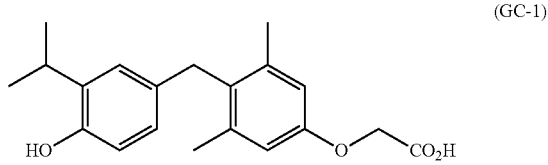 [SMILES: Cc1cc(OCC(=O)O)cc(C)c1Cc1ccc(O)c(C(C)C)c1]

(GC-1)

GC-1 is a thyromimetic, high affinity agonist at thyroid hormone receptor (TR) β and TRα receptors ($K_D$ values are 67 and 440 pM respectively). GC-1 displays 5- and 100-fold greater potency than the endogenous agonist $T_3$ in vitro at $TR\alpha_1$ and $TR\beta_1$ receptors respectively.

An effective amount of the thyroid hormone signaling pathway activator in the first medium and/or second medium comprises a concentration of about 0.1 μM to about 110 μM. In accordance with aspects of the present invention, the effective amount of the thyroid hormone signaling pathway activator in the first medium and/or second medium is a concentration of about 0.1 μM. In accordance with aspects of the present invention, the first medium and/or second medium is supplemented with about 0.1 μM to about 110 μM of GC-1. In accordance with aspects of the present invention, the first medium and/or second medium is supplemented with about 1 μM of GC-1.

Protein Kinase Inhibitor

The first medium and/or second medium may be supplemented with effective amounts of a protein kinase inhibitor.

Exemplary protein kinase inhibitor include, without limitation, staurosporine, an analog of staurosporine, such as Ro-31-8220, a bisindolylmaleimide (Bis) compound, 10'-{5"-[(methoxycarbonyl)amino]-2"-methyl}-phenylaminocarbonylstaurosporine, a staralog (see, e.g., Lopez et al., "Staurosporine-derived inhibitors broaden the scope of analog-sensitive kinase technology", *J. Am. Chem. Soc.* 2013; 135(48):18153-18159), and cgp41251. In accordance with aspects of the present invention, the first chemically defined, serum free medium is supplemented with staurosporine.

An effective amount of the protein kinase inhibitor for use in the first medium and/or second medium comprises a concentration of about 1 nM to about 1000 nM. In accordance with aspects of the present invention, the effective amount of the protein kinase inhibitor for use in the first medium and/or second medium comprises a concentration of 3 nM. In accordance with aspects of the present invention, the effective amount of staurosporine for use in the first medium and/or second medium comprises a concentration of between about 1 nM to about 1000 nM. In accordance with aspects of the present invention, the effective amount of staurosporine for use in the first medium and/or second medium comprises a concentration of about 3 nM.

Insulin

The first medium may be supplemented with effective amounts of insulin. The present invention contemplates any source of insulin (e.g., human, animal, etc.), as well as functional fragments of insulin. In accordance with some aspects, the first chemically defined, serum free medium is supplemented with an insulin receptor agonist or an agent that increases insulin secretion in the population of cells.

In accordance with aspects of the present invention, the effective amount of insulin comprises a concentration of between about 1 nM to about 1000 nM. In accordance with aspects of the present invention, the effective amount of insulin comprises a concentration of about 20 nM.

Heparin

The first medium and/or second medium may be supplemented with effective amounts of heparin. In accordance with aspects of the present invention, the effective amount of heparin in the first medium and/or second medium comprises a concentration of between about 1 µg/ml to about 100 µg/ml. In accordance with aspects of the present invention, the effective amount of heparin in the first medium and/or second medium comprises a concentration of about 10 µg/ml.

Antioxidant

The first medium may be supplemented with an effective amount of an antioxidant, e.g., a water soluble antioxidant. Exemplary antioxidants include Vitamin E, ascorbic acid, Vitamin C, and Trolox (a water soluble Vitamin E analog), disodium 4,5-dihydroxy-1,3-benzenedisulfonate (Tiron), and combinations thereof. In accordance with aspects of the present invention, the first chemically defined, serum free medium is supplemented with 6-hydroxy-2,5,7,8-tetramethylchroman-2-carboxylic acid (Trolox).

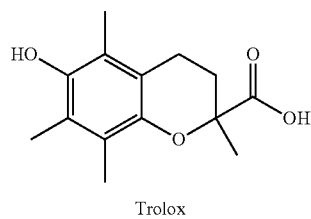 [SMILES: Cc1c(C)c2c(c(C)c1O)CCC(C)(C(=O)O)O2]

Trolox

The effective amount of antioxidant comprises a concentration of between about 0.1 µM to about 110 µM. In accordance with aspects of the present invention, the effective amount of antioxidant comprises a concentration of about 10 µM. In accordance with aspects of the present invention, the effective amount of Trolox comprises a concentration of between about 0.1 µM to about 110 µM. In accordance with aspects of the present invention, the effective amount of Trolox comprises a concentration of about 10 µM.

Epidermal Growth Factor (EGF) Family Growth Factor

The second medium may be supplemented with effective amounts of an epidermal growth factor family growth factor. Exemplary EGF family growth factors include, without limitation, betacellulin, EGF or a functional variant or fragment thereof, such as an isolated epidermal growth factor polypeptide having at least 90% amino acid identity to the human wild-type EGF polypeptide sequence, as disclosed in U.S. Pat. No. 7,084,246, an engineered EGF mutant that binds to and agonizes the EGF receptor, as is disclosed in U.S. Pat. No. 8,247,531. In accordance with aspects of the present invention, the EGF family growth factor comprises betacellulin.

An effective amount of EGF family growth factor for use in the second medium comprises a concentration of between about 1 ng/ml and about 1000 ng/ml. In accordance with aspects of the present invention, an effective amount of EGF family growth factor for use in the second medium comprises a concentration of 20 ng/ml. In accordance with aspects of the present invention, an effective amount of betacellulin for use in the second medium comprises a concentration of between about 1 ng/ml and about 1000 ng/ml. In accordance with aspects of the present invention, an effective amount of betacellulin for use in the second medium comprises a concentration of 20 ng/ml.

Retinoic Acid (RA) Signaling Pathway Activator

The second medium, the third medium, and/or the fourth medium may be supplemented with retinoic acid signaling pathway activator. Exemplary retinoic acid signaling pathway activators include, without limitation, retinoic acid, retinoic acid receptor agonists, such as CD 1530, AM 580, TTNPB, CD 437, Ch 55, BMS 961, AC 261066, AC 55649, AM 80, BMS 753, tazarotene, adapalene, and CD 2314.

An effective amount of retinoic acid signaling pathway activator for use in the second medium, the third medium, and/or the fourth medium comprises a concentration of between 1 nM and 110 µM. In accordance with aspects of the present invention, an effective amount of retinoic acid signaling pathway activator for use in the second medium comprises a concentration of 50 nM. In accordance with aspects of the present invention, an effective amount of retinoic acid signaling pathway activator for use in the third medium comprises a concentration of 100 nM. In accordance with aspects of the present invention, an effective amount of retinoic acid signaling pathway activator for use in the fourth medium comprises a concentration of 2 µM. In accordance with aspects of the present invention, an effective amount of RA for use in the second medium, the third medium, and/or the fourth medium comprises a concentration of between 1 nM and 110 µM. In accordance with aspects of the present invention, an effective amount of RA for use in the second medium comprises a concentration of 50 nM. In accordance with aspects of the present invention, an effective amount of RA for use in the third medium comprises a concentration of 100 nM. In accordance with aspects of the present invention, an effective amount of RA signaling pathway activator for use in the fourth medium comprises a concentration of 2 µM.

Sonic Hedgehog (SHH) Signaling Pathway Inhibitor

The second medium, third medium, and/or fourth medium may be supplemented with an effective amount of a SHH signaling pathway inhibitor. Exemplary SHH pathway inhibitors include, without limitation, SANT1, SANT2, SANT3, SANT4, Cur61414, forskolin, tomatidine, AY9944, triparanol, compound A or compound B (as disclosed in U.S. Pub. No. 2004/0060568), a steroidal alkaloid that antagonizes hedgehog signaling (e.g., cyclopamine or a derivative thereof) as disclosed in U.S. Pub. No. 2006/0276391. In accordance with aspects of the present invention, the SHH signaling pathway inhibitor comprises SANT1.

An effective amount of SHH signaling pathway inhibitor for use in the second medium, third medium, and/or fourth medium comprises a concentration of between about 0.1 µM and about 110 µM. In accordance with aspects of the present invention, an effective amount of SHH signaling pathway inhibitor for use in the second medium, third medium, and/or fourth medium comprises a concentration of between about 0.25 µM. In accordance with aspects of the present invention, an effective amount of SANT1 for use in the second medium, third medium, and/or fourth medium comprises a concentration of between about 0.1 µM and about 110 µM. In accordance with aspects of the present invention, an effective amount of SANT1 for use in the second medium, third medium, and/or fourth medium comprises a concentration of between about 0.25 µM.

Bone Morphogenic Protein (BMP) Signaling Pathway Inhibitor

In accordance with aspects of the present invention, the second medium and/or the fourth medium may be supplemented with effective amounts of a BMP signaling pathway inhibitor. The BMP signaling family is a diverse subset of the TGF-β superfamily (Sebald et al. Biol. Chem. 385:697-710, 2004). Over twenty known BMP ligands are recognized by three distinct type II (BMPRII, ActRIIa, and ActRIIb) and at least three type I (ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR–) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner (Nohe et al. Cell Signal 16:291-299, 2004). Soluble BMP antagonists such as noggin, chordin, gremlin, and follistatin limit BMP signaling by ligand sequestration.

Exemplary BMP signaling pathway inhibitors include, without limitation, 4-[6-(4-piperazin-1-ylphenyl)pyrazolo[1,5-a]pyrimidin-3-yl]quinolone (LDN 193189; also known as LDN193189, 1062368-24-4, LDN-193189, DM 3189, DM-3189, and referred to herein as LDN), an analog or derivative of LDN 193189, e.g., a salt (e.g., LDN193189 hydrochloride), hydrate, solvent, ester, or prodrug of LDN 193189, or a compound of Formula I from U.S. Patent Publication No. 2011/0053930. In accordance with aspects of the present invention, the BMP signaling pathway inhibitor comprises LDN 193189.

An effective amount of BMP signaling pathway inhibitor for use in the second medium and/or fourth medium comprises a concentration of between about 1 nM and 1000 nM. In accordance with aspects of the present invention, the effective amount of BMP signaling pathway inhibitor for use in the second medium and/or fourth medium comprises a concentration of 100 nM. In accordance with aspects of the present invention, the effective amount of LDN193189 for use in the second medium and/or fourth medium comprises a concentration of between 1 nM and 1000 nM. In accordance with aspects of the present invention, the effective amount of LDN193189 for use in the second medium and/or fourth medium comprises a concentration of 100 nM.

γ-Secretase Inhibitor

The second medium may be supplemented with effective amounts of a γ-secretase inhibitor. Exemplary γ-secretase inhibitors include, without limitation, XXI, DAPT, and a γ-secretase inhibitors described in U.S. Pat. Nos. 7,049,296, 8,481,499, 8,501,813, and WIPO Pub. No. WO/2013/052700. In accordance with aspects of the present invention, the γ-secretase inhibitor comprises XXI.

An effective amount of γ-secretase inhibitor for use in the second medium comprises a concentration of between about 0.1 µM and about 110 µM. In accordance with aspects of the present invention, the effective amount of γ-secretase inhibitor for use in the second medium comprises a concentration of about 1 µM. In accordance with aspects of the present invention, an effective amount of XXI for use in the second medium comprises a concentration of between about 0.1 µM and about 110 µM. In accordance with aspects of the present invention, the effective amount of XXI for use in the second medium comprises a concentration of about 1 µM.

Rock Inhibitor (Second Medium, Third Medium, Fourth Medium)

The second medium, third medium, and/or fourth medium may be supplemented with an effective amount of an inhibitor of rho-associated protein kinase (ROCK) (also referred to herein as ROCK inhibitor). Exemplary ROCK inhibitors include, but are not limited to a small organic molecule ROCK inhibitor selected from the group consisting of N-[(1S)-2-Hydroxy-1-phenylethyl]-V-[4-(4-pyridinyl)phenyl]-urea (AS1892802), fasudil hydrochloride (also known as HA 1077),-[3-[[2-(4-Amino-1,2,5-oxadiazol-3-yl)-1-ethyl-1H-imidazo[4,5-c]pyridin-6-yl]oxy]phenyl]-4-[2-(4-morpholinyl)ethoxy]benzamide (GSK269962), 4-[4-(Trifluoromethyl)phenyl]-N-(6-Fluoro-1H-indazol-5-yl)-2-methyl-6-oxo-1,4,5,6-tetrahydro-3-pyridinecarboxamide (GSK 429286), (S)-(+)-2-Methyl-1-[(4-methyl-5-isoquinolinyl)sulfonyl]-hexahydro-1H-1,4-diazepine dihydrochloride (H 1152 dihydrochloride), (S)-(+)-4-Glycyl-2-methyl-1-[(4-methyl-5-isoquinolinyl)sulfonyl]-hexahydro-1H-1,4-diazepine dihydrochloride (glycyl-H 1152 dihydrochloride), N-[(3-Hydroxyphenyl)methyl]-V-[4-(4-pyridinyl)-2-thiazolyl]urea dihydrochloride (RKI 1447 dihydrochloride), (3S)-1-[[2-(4-Amino-1,2,5-oxadiazol-3-yl)-1-ethyl-1H-imidazo[4,5-c]pyridin-7-yl]carbonyl]-3-pyrrolidinamine dihydrochloride (SB772077B dihydrochloride), N-[2-[2-(Dimethylamino)ethoxy]-4-(1H-pyrazol-4-yl)phenyl-2,3-dihydro-1,4-benzodioxin-2-carboxamide dihydrochloride (SR 3677 dihydrochloride), and trans-4-[(1R)-1-Aminoethyl]-N-4-pyridinylcyclohexanecarboxamide dihydrochloride (Y-27632 dihydrochloride), N-Benzyl-[2-(pyrimidin-4-yl)amino]thiazole-4-carboxamide (Thiazovivin), Rock Inhibitor, a isoquinolinesulfonamide compound (Rho Kinase Inhibitor), N-(4-Pyridyl)-N'-(2,4,6-trichlorophenyl) urea (Rho Kinase Inhibitor II), 3-(4-Pyridyl)-1H-indole (Rho Kinase Inhibitor III, Rockout), and 4-pyrazoleboronic acid pinacol ester; a Rock antibody commercially available from Santa Cruz Biotechnology selected from the group consisting of Rock-1 (B1), Rock-1 (C-19), Rock-1 (H-11), Rock-1 (G-6), Rock-1 (H-85), Rock-1 (K-18), Rock-2 (C-20), Rock-2 (D-2), Rock-2 (D-11), Rock-2 (N-19), Rock-2 (H-85), Rock-2 (30-J); a ROCK CRISPR/Cas9 knockout plasmid selected from the group consisting of Rock-1 CRISPR/Cas9 KO plasmid (h), Rock-2 CRISPR/Cas9 KO plasmid (h), Rock-1 CRISPR/Cas9 KO plasmid (m), Rock-2 CRISPR/Cas9 KO plasmid (m); a ROCK siRNA, shRNA plasmid and/or shRNA lentiviral particle gene silencer selected from the group consisting of Rock-1 siRNA (h): sc-29473, Rock-1 siRNA (m): sc-36432, Rock-1 siRNA (r): sc-72179, Rock-2 siRNA (h): sc-29474, Rock-2 siRNA (m): sc-36433, Rock-2 siRNA (r): sc-108088. In accordance with aspects of the present invention, the ROCK inhibitor comprises Y-27632.

An effective amount of ROCK inhibitor for use in the second medium, third medium, and/or fourth medium comprises a concentration of between 0.1 µM and 110 µM. In accordance with aspects of the present invention, an effective amount of ROCK inhibitor for use in the second medium, third medium, and/or fourth medium comprises a concentration of 10 µM. In accordance with aspects of the present invention, an effective amount of Y-27632 for use in the second medium, third medium, and/or fourth medium comprises a concentration of between 0.1 µM and 110 µM. In accordance with aspects of the present invention, an effective amount of Y-27632 for use in the second medium, third medium, and/or fourth medium comprises a concentration of 10 µM.

Fibroblast Growth Factor (FGF) Family Growth Factor

The third medium, fourth medium, and/or fifth medium may be supplemented with effective amounts of a FGF family growth factor. Exemplary FGF family growth factors include, without limitation, keratinocyte growth factor (KGF) (GenBank Accession AAB21431), FGF2 (GenBank Accession NP_001997), FGF8B (GenBank Accession AAB40954), FGF10 (GenBank Accession CAG46489), FGF21 (GenBank Accession AAQ89444.1), and functional fragments of any thereof. In accordance with aspects of the present invention, the FGF family growth factor comprises KGF.

An effective amount of FGF family growth factor for use in the third medium, fourth medium, and/or fifth medium comprises a concentration of between 1 ng/ml and 1000 ng/ml. In accordance with aspects of the present invention, the effective amount of FGF family growth factor for use in the third medium, fourth medium, and/or fifth medium comprises a concentration of 50 ng/ml. In accordance with aspects of the present invention, the effective amount of KGF for use in the third medium, fourth medium, and/or fifth medium comprises a concentration of between 1 ng/ml and 1000 ng/ml. In accordance with aspects of the present invention, the effective amount of KGF for use in the third medium, fourth medium, and/or fifth medium comprises a concentration of 50 ng/ml.

TGFβ Superfamily Member

In accordance with aspects of the present invention, the third medium and/or sixth medium may be supplemented with effective amounts of a TGFβ superfamily member. The "TGF-β superfamily" means proteins having structural and functional characteristics of known TGFβ family members. The TGFβ family of proteins is well characterized, both from structural and functional aspects. It includes the TGFβ series of proteins, the Inhibins (including Inhibin A and Inhibin B), the Activins (including Activin A, Activin B, and Activin AB), MIS (Müllerian inhibiting substance), BMP (bone morphogenetic proteins), dpp (decapentaplegic), Vg-1, MNSF (monoclonal nonspecific suppressor factor), and others. Activity of this family of proteins is based on specific binding to certain receptors on various cell types. Members of this family share regions of sequence identity, particularly at the C-terminus, that correlate to their function. The TGFβ family includes more than one hundred distinct proteins, all sharing at least one region of amino acid sequence identity. The TGF-β superfamily member (i.e., growth factor) can be naturally obtained or recombinant.

Exemplary TGFβ superfamily members include, without limitation, growth differentiation factor 8 (GDF8) (GenBank Accession EAX10880), growth differentiation factor 11 (GDF11) (GenBank Accession AAF21630), Activin A, Nodal, Activin A, Activin B, bone morphogenic protein-2 (BMP2), bone morphogenic protein-4 (BMP4), and functional fragments of any thereof. In some aspects, the TGFβ superfamily member can be replaced with an agent that mimics growth factors from the TGF-β superfamily, such as IDE1 and IDE2

In accordance with aspects of the present invention, the TGF-β superfamily member comprises Activin A. The term "Activin A" includes fragments and derivatives of Activin A. The sequence of an exemplary Activin A is disclosed as SEQ ID NO: 1 in U.S. Pub. No. 2009/0155218 (the '218 publication'). Other non-limiting examples of Activin A are provided in SEQ ID NO: 2-16 of the '218 publication, and non-limiting examples of nucleic acids encoding Activin A are provided in SEQ ID NO:33-34 of the '218 publication, and functional fragments thereof. An effective amount of the TGF-β superfamily member for use in the third medium and/or sixth medium comprises a concentration of about 1 ng/ml to about 1000 ng/ml. In accordance with aspects of the present invention, the effective amount of the TGF-β superfamily member for use in the third medium and/or sixth medium comprises a concentration of 5 ng/ml. In accordance with aspects of the present invention, the effective amount of the TGF-β superfamily member for use in the third medium and/or sixth medium comprises a concentration of 100 ng/ml. In accordance with aspects of the present invention, the effective amount of Activin A for use in the third medium is about 5 ng/ml. In accordance with aspects of the present invention, the effective amount of Activin A for use in the sixth medium comprises a concentration of about 100 ng/ml/

Protein Kinase C (PKC) Activator

The fourth medium may be supplemented with effective amounts of a protein kinase C (PKC) activator. Protein kinase C is one of the largest families of protein kinase enzymes and is composed of a variety of isoforms. Conventional isoforms include a, βI, βII, γ; novel isoforms include δ, ε, η, Θ; and atypical isoforms include ξ, and ι/λ. PKC enzymes are primarily cytosolic but translocate to the membrane when activated. In the cytoplasm, PKC is phosphorylated by other kinases or autophosphorylates. In order to be activated, some PKC isoforms (e.g., PKC-ε) require a molecule to bind to the diacylglycerol ("DAG") binding site or the phosphatidylserine ("PS") binding site. Others are able to be activated without any secondary binding messengers at all. PKC activators that bind to the DAG site include, but are not limited to, bryostatin, picologues, phorbol esters, aplysiatoxin, and gnidimacrin. PKC activators that bind to the PS site include, but are not limited to, polyunsaturated fatty acids and their derivatives. It is contemplated that any protein kinase C activator that is capable, either alone or in combination with one or more other β cell maturation factors, of inducing the differentiation of at least one insulin-producing, endocrine cell or precursor thereof into a SC-β cell can be used in the methods, compositions, and kits described herein.

Exemplary PKC activators include, without limitation, PdbU, TPB, cyclopropanated polyunsaturated fatty acids, cyclopropanated monounsaturated fatty acids, cyclopropanated polyunsaturated fatty alcohols, cyclopropanated monounsaturated fatty alcohols, cyclopropanated polyunsaturated fatty acid esters, cyclopropanated monounsaturated fatty acid esters, cyclopropanated polyunsaturated fatty acid sulfates, cyclopropanated monounsaturated fatty acid sulfates, cyclopropanated polyunsaturated fatty acid phosphates, cyclopropanated monounsaturated fatty acid phosphates, macrocyclic lactones, DAG derivatives, isoprenoids, octyl-indolactam V, gnidimacrin, iripallidal, ingenol, napthalenesulfonamides, diacylglycerol kinase inhibitors, fibroblast growth factor 18 (FGF-18), insulin growth factor, hormones, and growth factor activators, as described in WIPO Pub. No. WO/2013/071282. In some aspects, the bryostain comprises bryostatin-1, bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, or bryostatin-18. In accordance with aspects of the present invention, the PKC activator comprises PdbU.

An effective amount of PKC activator for use in the fourth medium comprises a concentration of between about 1 nM and 1000 nM. In accordance with aspects of the present invention, an effective amount of PKC activator for use in the fourth medium comprises a concentration of between about 500 nM. In accordance with aspects of the present invention, an effective amount of PdbU for use in the fourth medium comprises a concentration of between about 1 nM and 1000 nM. In accordance with aspects of the present invention, an effective amount of PdbU for use in the fourth medium comprises a concentration of between about 500 nM.

WNT Signaling Pathway Activator

The sixth medium may be supplemented with effective amounts of a WNT signaling pathway activator. Exemplary WNT signaling pathway activators include, without limitation, CHIR99021, derivatives of CHIR99021, e.g., a salt of CHIR99021, e.g., trihydrochloride, a hydrochloride salt of CHIR99021, Wnt3a recombinant protein, a glycogen synthase kinase 3 (GSK3) inhibitor, such as 3F8, A 1070722, AR-A 014418, BIO, BIO-acetoxime, FRATide, 10Z-Hymenialdisine, Indirubin-3'oxime, kenpaullone, L803, L803-mts, lithium carbonate, NSC 693868, SB 216763, SB 415286, TC-G 24, TCS 2002, TCS 21311, TWS 119, and analogs or derivatives of any of these.

An effective amount of the WNT signaling pathway activator for use in the sixth medium comprises a concentration of between about 0.1 µM and about 110 µM. In accordance with aspects of the present invention, the effective amount of the WNT signaling pathway activator comprises a concentration of 3 µM. In accordance with aspects of the present invention, the effective amount of CHIR99021 comprises a concentration of between about 0.1 µM and 110 µM. In accordance with aspects of the present invention, the effective amount of CHIR99021 comprises a concentration of 3 µM.

SC-β Cells Obtained by the Method of Generating SC-β Cells

In accordance with an embodiment of the present invention, an isolated SC-β cell or population thereof generated according to a method described herein is provided. The isolated SC-β cell or population exhibits a GSIS response both in vitro and in vivo. The isolated SC-β cell or population also exhibits at least one characteristic feature of a mature endogenous β cell (e.g., monohormonality). In some aspects, an isolated SC-β cell or population thereof exhibits a stimulation index of between about 1.4 and about 3.0. In some aspects, an isolated SC-β cell or population thereof produces between approximately 300 uIU to about 4000 uIU per 30 minute per $10^6$ total cells incubation at a high glucose concentration.

The SC-β cells disclosed herein share many distinguishing features of native β cells, but are different in certain aspects (e.g., gene expression profiles). In some embodiments, the SC-β cell is non-native. As used herein, "non-native" means that the SC-β cells are markedly different in certain aspects from β cells which exist in nature, i.e., native β cells. It should be appreciated, however, that these marked differences typically pertain to structural features which may result in the SC-β cells exhibiting certain functional differences, e.g., although the gene expression patterns of SC-β cells differs from native β cells, the SC-β cells behave in a similar manner to native β cells but certain functions may be altered (e.g., improved) compared to native β cells. For example, a higher frequency of SC-β cells respond to 20 mM glucose compared to the frequency of native β cells. Other differences between SC-β cells and native β cells would be apparent to the skilled artisan based on the data disclosed herein.

The SC-β cells (e.g., human) generated according to the methods described herein may exhibit at least one of the following characteristics of an endogenous mature pancreatic β cell: i) a response to multiple glucose challenges that resembles the response of endogenous islets (e.g., at least one, at least two, or at least three or more sequential glucose challenges); ii) a morphology that resembles the morphology of an endogenous β cell; iii) packaging of insulin into secretory granules or encapsulated crystalline insulin granules; iv) a stimulation index of greater than at least 1.4; v) cytokine-induced apoptosis in response to cytokines; vi) enhanced insulin secretion in response to known antidiabetic drugs (e.g., secretagogues); vii) monohormonal, i.e., they do not abnormally co-express other hormones, such as glucagon, somatostatin or pancreatic polypeptide; viii) a low rate of replication; and ix) increased intracellular $Ca^{2+}$ in response to glucose. In accordance with an embodiment of the present invention, a microcapsule comprising the isolated SC-β cell or population thereof encapsulated therein is provided.

In accordance with an embodiment of the present invention, a macroencapsulation device comprising the isolated SC-β cell or population thereof is provided.

In accordance with an embodiment of the present invention, a cell line comprising an isolated SC-β cell that stably expresses insulin is provided.

Assays

In accordance with an embodiment of the present invention, an isolated SC-β cell or population thereof generated according to the methods herein, or an SC-β cell that stably expresses insulin, can be used in various assays. In some aspects, an isolated SC-β cell, population thereof, or an SC-β cell that stably expresses insulin, can be used in an assay to identify one or more candidate agents which promote or inhibit a β cell fate selected from the group consisting of β cell proliferation, β cell replication, β cell death, β cell function, β cell susceptibility to immune attack, and β cell susceptibility to dedifferentiation or differentiation. In some aspects, an isolated SC-β cell, population thereof, or an SC-β cell that stably expresses insulin, can be used in an assay to identify one or more candidate agents which promote the differentiation of at least one insulin-positive endocrine cell or a precursor thereof into at least one SC-β cell. The assays typically involve contacting the isolated SC-β cell, population thereof, or an SC-β cell that stably expresses insulin, with one or more candidate agents to be assessed for its ability to i) promote or inhibit a β cell fate selected from the group consisting of β cell proliferation, β cell replication, cell death, β cell function, β cell susceptibility to immune attack, and cell susceptibility to dedifferentiation or differentiation, or ii) promoting the differentiation of at least one insulin-positive endocrine cell or a precursor thereof into at least one SC-β cell and assessing whether the candidate agent possesses the ability to i) promote or inhibit a α cell fate selected from the group consisting of β cell proliferation, β cell replication, β cell death, β cell function, β cell susceptibility to immune attack, and β cell susceptibility to dedifferentiation or differentiation, or ii) promoting the differentiation of at least one insulin-positive endocrine cell or a precursor thereof into at least one SC-β cell.

Methods for Treatment

In accordance with an embodiment of the present invention, methods for the treatment of a subject in need thereof are provided. The methods entail administering to a subject in need thereof an isolated population of SC-β cells or a microcapsule comprising SC-β cells encapsulated therein. In some aspects, the subject is in need of additional β cells. In some aspects, the subject has, or has an increased risk of developing diabetes. A SC-β cell or population (e.g., isolated) of SC-β cells generated by a method of the present invention can be administered to a subject for treatment of type 1 or type 2 diabetes. In some aspects, the subject has, or has an increased risk of developing, a metabolic disorder. In some aspects, administering to the subject comprises implanting SC-β cells, a microcapsule comprising SC-β cells, or a macroencapsulation device comprising SC-β cells into the subject. The subject may be a human subject or an animal subject. In some aspects, the cells may be implanted as dispersed cells or formed into clusters that may be infused into the hepatic portal vein. In some aspects, cells may be provided in biocompatible degradable polymeric supports, porous non-degradable devices or encapsulated to protect from host immune response. Cells may be implanted into an appropriate site in a recipient. The implantation sites include, for example, the liver, natural pancreas, renal subcapsular space, omentum, peritoneum, subserosal space, intestine, stomach, or a subcutaneous pocket.

To enhance further differentiation, survival or activity of the implanted cells in vivo, additional factors, such as growth factors, antioxidants or anti-inflammatory agents, can be administered before, simultaneously with, or after the administration of the cells. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In some aspects, the method of treatment further comprises incorporating the cells into a three-dimensional support prior to implantation. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Artificial Islet or Pancreas

In accordance with an embodiment of the present invention, an artificial islet or pancreas is provided. The artificial islet or pancreas can be constructed using the SC-β cells generated according to the methods described herein.

An artificial pancreas is a device that encapsulates and nurtures islets of Langerhans to replace the islets and β cells destroyed by type 1 diabetes. An artificial pancreas may contain a million islets or more, and may be implanted in the peritoneal cavity or under the skin where it can respond to changing blood glucose levels by releasing hormones, such as insulin. An artificial pancreas may be made using living (e.g., glucose-sensing and insulin secreting islets) and non-living components (e.g., to shield the islets from the diabetic's body and its destructive immune mechanism while permitting the islets to thrive).

The present invention contemplates using β cells in any artificial pancreas. In some aspects, the artificial pancreas comprises microencapsulated or coated islets comprising SC-β cells generated according to the methods herein. In some aspects, the artificial pancreas comprises a macroencapsulation device into which islet cells comprising SC-β cells generated according to the methods herein are grouped together and encapsulated. In some aspects, the macroencapsulation device comprises a PVA hydrogel sheet for an artificial pancreas of the present invention (Qi et al., 2004). In some aspects, the artificial islet comprises SC-β cells generated according to the methods herein, along with other islet cells (α, δ, etc.) in the form of an islet sheet. The islet sheet comprises a layer of artificial human islets comprising the SC-β cells macroencapsulated within a membrane (e.g., of ultra-pure alginate). The sheet membrane is reinforced with mesh and may be coated on the surface to prevent or minimize contact between the cells encapsulated inside and the transplantation recipient's host immune response. Oxygen, glucose, and other nutrients readily diffuse into the sheet through the membrane nurturing the islets, and hormones, such as insulin readily diffuse out. Additional examples of membranes designed for macroencapsulation/implantation of an artificial islet or pancreas can be found in the literature (Isayeva et al. 2003). Another example of a macroencapsulated implant suitable for an artificial islet or pancreas can be found in the literature (Aurélien, et al. 2014).

Terminology

The articles "a", "an" and "the" as used herein, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. It should also be understood that any embodiment of the invention, e.g., any embodiment found within the prior art, can be explicitly excluded from the claims, regardless of whether the specific exclusion is recited in the specification. For example, any agent may be excluded from the set of factors, small molecules, basal media components, or supplemental media components in any step of the differentiation protocols described herein.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% of a number in either direction (greater than or less than the number) unless otherwise stated or otherwise evident from the context (except where such number would impermissibly exceed 100% of a possible value).

Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group.

Certain claims are presented in dependent form for the sake of convenience, but any dependent claim may be rewritten in independent format to include the limitations of the independent claim and any other claim(s) on which such claim depends, and such rewritten claim is to be considered equivalent in all respects to the dependent claim (either amended or unamended) prior to being rewritten in independent format. It should also be understood that, unless clearly indicated to the contrary, in any methods claimed herein that include more than one act, the order of the acts of the method is not necessarily limited to the order in which the acts of the method are recited, but the invention includes embodiments in which the order is so limited. It is contemplated that all aspects described above are applicable to all different embodiments of the invention. It is also contemplated that any of the above embodiments can be freely combined with one or more other such embodiments whenever appropriate.

As used herein, "first", "second", "third", "fourth", "fifth" and "sixth" in the context of a "chemically defined, serum free medium" refers to the order in which the chemically defined, serum free medium appears in the claims and is in no way intended to impart or limit the order in which the chemically defined, serum free medium is employed during the six stage differentiation protocol.

REFERENCES

1. Bellin et al., (2012). Potent induction immunotherapy promotes long-term insulin independence after islet transplantation in type 1 diabetes. Am. J. Transplant. 12, 1576-1583.
2. Pagliuca et al. (2014). Generation of Functional Human Pancreatic β cells In Vitro. Cell. 159, 428-439.
3. Rezania et al. (2014). Reversal of diabetes with insulin-producing cells derived in vitro from human pluripotent stem cells. Nat. Biotech. 32(11), 1121-1133.
4. Isayeva, et al. (2003). Characterization and performance of membranes designed for macroencapsulation/implantation of pancreatic islet cells. Biomaterials 24(20), 3483-3491.
5. Motté, et al. (2014). Composition and function of macroencapsulated human embryonic stem cell-derived implants: comparison with clinical human islet cell grafts. American Journal of Physiology-Endocrinology and Metabolism 307(9), E838-E846.
6. Qi et al. (2004). PVA hydrogel sheet macroencapsulation of the bioartificial pancreas. *Biomaterials* 24(27), 5885-5892.

What is claimed is:

1. A serum free in vitro composition that comprises a ROCK inhibitor, a BMP signaling pathway inhibitor, a gamma secretase inhibitor, and a plurality of pancreatic progenitor cells that express PDX1 and NKX6.1.

2. The composition of claim 1, wherein the composition further comprises insulin-expressing cells.

3. The composition of claim 1, wherein the ROCK inhibitor is a small molecule inhibitor.

4. The composition of claim 1, wherein the ROCK inhibitor is selected from the group consisting of: AS 1892802, GSK 429286, RKI-1147 dihydrochloride, SB772077B dihydrochloride, SR 3677 dihydrochloride, Rho Kinase Inhibitor, Rho Kinase Inhibitor II, Rho Kinase Inhibitor III, thiazovivin, Y-27632, Fasudil hydrochloride, and H-1152 dihydrochloride.

5. The composition of claim 1, wherein the ROCK inhibitor is thiazovivin.

6. The composition of claim 1, wherein the ROCK inhibitor is Y-27632.

7. The composition of claim 1, wherein the composition comprises from 0.1 μM to 110 μM of the ROCK inhibitor.

8. The composition of claim 1, wherein the pancreatic progenitor cells that express PDX1 and NKX6.1 are human cells.

9. The composition of claim 1, wherein the composition further comprises one or more of a retinoic acid signaling pathway activator, a sonic hedgehog pathway inhibitor, and a TGF-beta pathway inhibitor.

10. The composition of claim 9, wherein the composition comprises two or more of the retinoic acid signaling pathway activator, the sonic hedgehog pathway inhibitor, and the TGF-beta pathway inhibitor.

11. The composition of claim 10, wherein the composition comprises the retinoic acid signaling pathway activator, the sonic hedgehog pathway inhibitor, and the TGF-beta pathway inhibitor.

12. The composition of claim 1, wherein the composition further comprises a retinoic acid signaling pathway activator.

13. The composition of claim 12, wherein the retinoic acid signaling pathway activator is selected from the group consisting of: retinoic acid, CD 1530, AM 580, TTNPB, CD 437, Ch 55, BMS 961, AC 261066, AC 55649, AM 80, BMS 753, tazarotene, adapalene, and CD 2314.

14. The composition of claim 1, wherein the composition further comprises a sonic hedgehog pathway inhibitor.

15. The composition of claim 14, wherein the sonic hedgehog pathway inhibitor is selected from the group consisting of: SANT1, SANT2, SANT3, SANT4, Cur61414, forskolin, tomatidine, AY9944, triparanol, and cyclopamine.

16. The composition of claim 1, wherein the composition further comprises a TGF-beta pathway inhibitor.

17. The composition of claim 16, wherein the TGF-beta pathway inhibitor is selected from the group consisting of: ALK5 inhibitor II; A83-01, 431542, D4476, GW788388, LY364947, LY 580276, SB 525334, SB 505124, SD 208, and GW 6604.

18. The composition of claim 1, wherein the BMP signaling pathway inhibitor is LDN 193189.

19. The composition of claim 11, wherein:
a) the BMP signaling pathway inhibitor is LDN193189;
b) the retinoic acid signaling pathway activator is selected from the group consisting of: retinoic acid, CD 1530, AM 580, TTNPB, CD 437, Ch 55, BMS 961, AC 261066, AC 55649, AM 80, BMS 753, tazarotene, adapalene, and CD 2314;
c) the sonic hedgehog pathway inhibitor is selected from the group consisting of: SANT1, SANT2, SANT3, SANT4, Cur61414, forskolin, tomatidine, AY9944, triparanol, and cyclopamine;
d) the TGF-beta pathway inhibitor is selected from the group consisting of: ALK5 inhibitor II; A83-01, 431542, D4476, GW788388, LY364947, LY 580276, SB 525334, SB 505124, SD 208, and GW 6604; and
e) the ROCK inhibitor is selected from the group consisting of: AS 1892802, GSK 429286, RKI-1147 dihydrochloride, SB772077B dihydrochloride, SR 3677 dihydrochloride, Rho Kinase Inhibitor, Rho Kinase Inhibitor II, Rho Kinase Inhibitor III, thiazovivin, Y-27632, Fasudil hydrochloride, and H-1152 dihydrochloride.

20. The composition of claim 11, wherein the BMP signaling pathway inhibitor comprises LDN193189, the retinoic acid signaling pathway activator comprises retinoic acid, the sonic hedgehog pathway inhibitor comprises SANT1, and the TGF-beta pathway inhibitor comprises Alk5 inhibitor II.

21. The method of claim 1, wherein the gamma secretase inhibitor comprises XXI.

22. The method of claim 20, wherein the gamma secretase inhibitor comprises XXI.

* * * * *